US009533172B2

(12) United States Patent
Sugiura et al.

(10) Patent No.: US 9,533,172 B2
(45) Date of Patent: Jan. 3, 2017

(54) IMAGE PROCESSING BASED ON POSITIONAL DIFFERENCE AMONG PLURAL PERSPECTIVE IMAGES

(71) Applicant: KABUSHIKI KAISHA TOSHIBA, Minato-ku, Tokyo (JP)

(72) Inventors: Kyoka Sugiura, Kanagawa (JP); Ryusuke Hirai, Tokyo (JP); Yukinobu Sakata, Kanagawa (JP); Yasunori Taguchi, Kanagawa (JP); Takeshi Mita, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 132 days.

(21) Appl. No.: 14/460,402

(22) Filed: Aug. 15, 2014

(65) Prior Publication Data

US 2015/0117605 A1 Apr. 30, 2015

(30) Foreign Application Priority Data

Oct. 31, 2013 (JP) .................................. 2013-227226

(51) Int. Cl.
*G06K 9/00* (2006.01)
*A61N 5/10* (2006.01)
*G06T 7/00* (2006.01)
*G06T 19/00* (2011.01)

(52) U.S. Cl.
CPC ............ *A61N 5/1049* (2013.01); *A61N 5/107* (2013.01); *G06T 7/0042* (2013.01); *G06T 19/00* (2013.01); *A61N 2005/1061* (2013.01); *G06T 2207/10116* (2013.01); *G06T 2210/41* (2013.01); *G06T 2219/028* (2013.01)

(58) Field of Classification Search
None
See application file for complete search history.

(56) References Cited

U.S. PATENT DOCUMENTS 9,122,065 B2 * 9/2015 Uehara .............. G02B 27/2214
9,223,160 B2 * 12/2015 Nishimura .......... G02F 1/13306
9,230,322 B2 * 1/2016 Hirai .................... G06T 7/0012
(Continued)

FOREIGN PATENT DOCUMENTS

JP 2011-212130 10/2011
JP 2015-019846 2/2015
JP 2015-029838 2/2015

*Primary Examiner* — Tahmina Ansari
(74) *Attorney, Agent, or Firm* — Nixon & Vanderhye, P.C.

(57) ABSTRACT

According to some embodiments, an image processor includes a perspective image generator, a perspective image acquirer, a corresponding point acquirer, a first calculator and a display image generator. The first calculator updates the position of the one or more first corresponding point on the first perspective image, based on a difference in position between the first and second perspective images. The display image generator generates a first display image including the first and second perspective images, the one or more first corresponding points updated on the first perspective image, and the one or more second corresponding points on the second perspective image. The perspective image generator changes the first direction into a third direction based on the difference in position between the first and second perspective images, and generates an updated one, viewed in the third direction, of the first perspective image.

18 Claims, 13 Drawing Sheets

(56) References Cited

U.S. PATENT DOCUMENTS

| | | | |
|---|---|---|---|
| 2011/0110487 A1* | 5/2011 | Fuchs | A61B 6/032 378/10 |
| 2012/0262362 A1* | 10/2012 | Uehara | G02B 27/2214 345/88 |
| 2012/0306849 A1* | 12/2012 | Steen | G06F 3/04815 345/419 |
| 2014/0104521 A1* | 4/2014 | Nishimura | G02F 1/13306 349/33 |
| 2015/0025295 A1* | 1/2015 | Sugiura | A61N 5/1049 600/1 |
| 2015/0045605 A1* | 2/2015 | Hirai | A61N 5/103 600/1 |
| 2015/0117605 A1* | 4/2015 | Sugiura | G06T 19/00 378/62 |

\* cited by examiner

IMAGE PROCESSING BASED ON POSITIONAL DIFFERENCE AMONG PLURAL PERSPECTIVE IMAGES

CROSS-REFERENCE TO RELATED APPLICATION

This application is based upon and claims the benefit of priority from Japanese Patent Application No. 2013-227226, filed Oct. 31, 2013; the entire contents of which are incorporated herein by reference.

FIELD

Embodiments described herein relate generally to an image processor, a treatment system, and an image processing method.

BACKGROUND

At the time of performing a radiotherapy treatment, an object to be treated is positioned at the previously-planned position. There is a method of positioning the object to be treated. For example, corresponding points are designated on a first image captured by radiography at the time of planning a treatment and on a second image captured by radiography at the time of actual treatment, and the object to be treated is positioned based on a difference in position between the corresponding points.

It is difficult to designate the corresponding points when the difference is large in posture of the object between at the planning time and at the treatment time.

DETAILED DESCRIPTION

Figure 1:
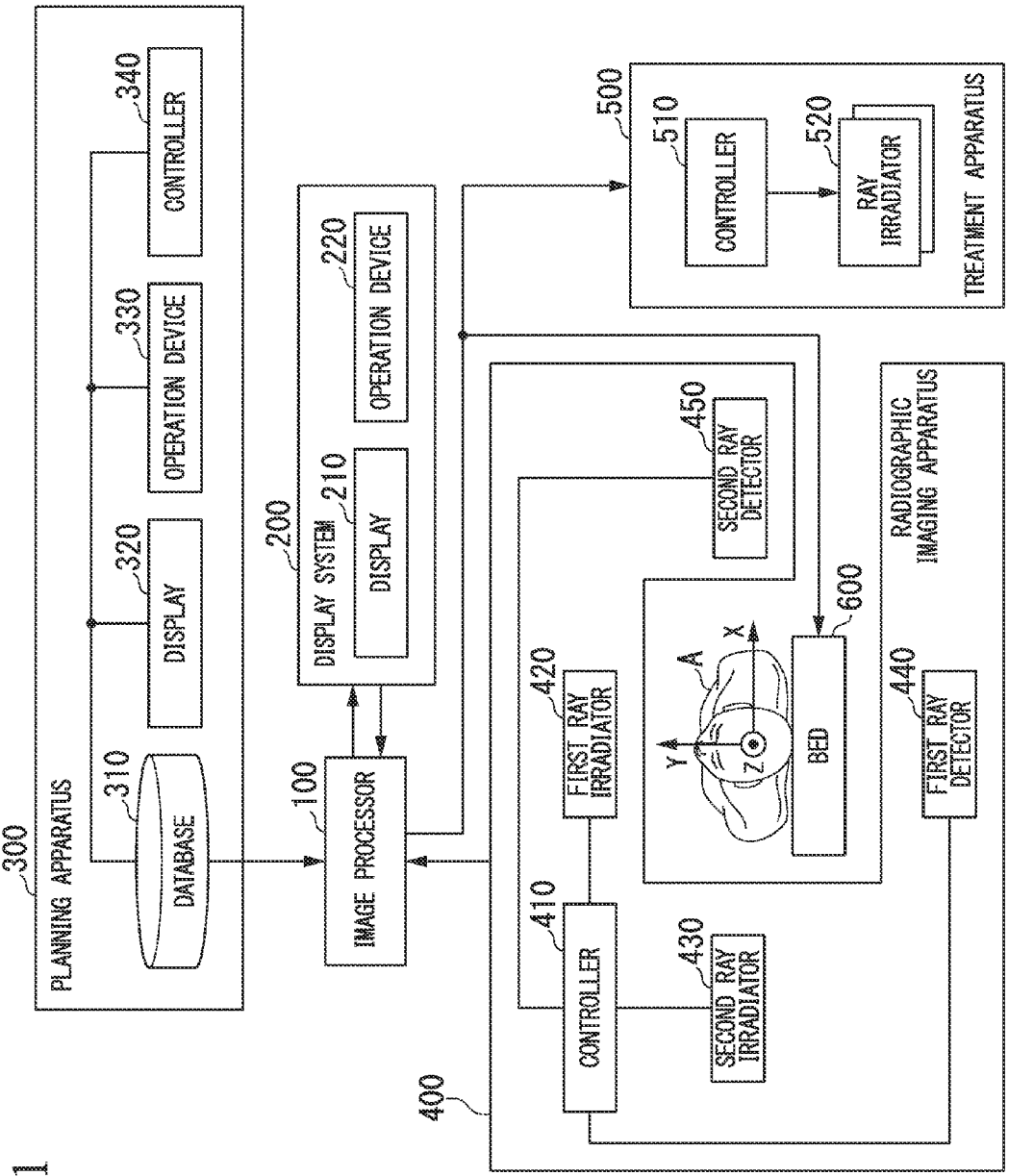
FIG. 1 is a block diagram illustrating an example of a treatment system according to a first embodiment.

According to some embodiments, an image processor may include, but is not limited to, a perspective image generator, a perspective image acquirer, a corresponding point acquirer, a first calculator, and a display image generator. The perspective image generator generates a first perspective image of a target viewed in a first direction, based on three-dimensional volume data of the target. The perspective image acquirer acquires a second perspective image of the target viewed in a second direction. The corresponding point acquirer acquires one or more pairs of first and second corresponding points respectively on the first and second perspective images. The first calculator updates the position of the one or more first corresponding points on the first perspective image, based on a difference in position between the first and second perspective images. The display image generator generates a first display image. The first display image may include, but is not limited to, the first and second perspective images, the one or more first corresponding points updated on the first perspective image, and the one or more second corresponding points on the second perspective image. The perspective image generator changes the first direction into a third direction based on the difference in position between the first and second perspective images, and generates an updated one, viewed in the third direction, of the first perspective image.

In some cases, the processor may further include, but is not limited to, a second calculator. The second calculator calculates the difference by calculating a difference in position between the three-dimensional volume data and the target at the time the second perspective image is captured before the second perspective image is acquired by the perspective image acquirer, based on the one or more first and second corresponding points of the first and second perspective images.

In some cases, the corresponding point acquirer acquires one or more pairs of third and fourth corresponding points respectively on the first and second perspective images. The second calculator updates the difference in position between the first and second perspective images, based on the one or more pairs of first and second corresponding points and the one or more pairs of third and fourth corresponding points. The first calculator updates the one or more first and third corresponding points, based on the difference updated lastly in position between the first and second perspective images. The display image generator generates an updated one of the first display image, the updated one includes the lastly updated one of the first display image including the first perspective image and the one or more first and third corresponding points, which are updated lastly, and the second perspective image.

In some cases, the second calculator updates the difference, based on one or more undeleted pairs of the first and second corresponding points acquired, when any corresponding points have been deleted.

In some cases, the corresponding point acquirer determines whether a designated corresponding point on one of the first and second perspective images is a modified corresponding point to which the existent one of the one or more first and second corresponding points or an additional corresponding point to be added to the existent ones of the one or more first and second corresponding points. The corresponding point acquirer deletes a closest existent one, to the designated corresponding point, of the one or more first and second corresponding points in a case that the corresponding point acquirer determines that the designated corresponding point is the modified corresponding point.

In some cases, the image processor may further include, but is not limited to, a corresponding point modifier that calculates a similarity between first and second partial images. The first partial image includes the first corresponding point which position has been last updated by the first calculator. The second partial image includes the second corresponding point which is paired with that first corresponding point. The corresponding point modifier detects a region having a highest similarity to the second partial image from the first perspective image, if the similarity calculated is smaller than a predetermined reference value. The corresponding point modifier modifies the position of the first corresponding point based on the region detected.

In some cases, the display image generator modifies, based on the difference, an epipolar line on the first perspective image. The epipolar line is associated with the one or more first corresponding points.

In some cases, the perspective image generator changes the third direction into a fourth direction based on the difference in position between the updated one, viewed in the third direction, of the first perspective image and the second perspective image. The perspective image generator generates a further updated one, viewed in the fourth direction, of the first perspective image.

According to other embodiments, a treatment system may include, but is not limited to, an image processor, an irradiator, a detector and a display system. The irradiator irradiates X-rays to a target. The detector detects X-rays transmitted through the target. The detector makes a second perspective image of the target viewed in a second direction based on the X-rays. The image processor may include, but is not limited to, a perspective image generator, a perspective image acquirer, a corresponding point acquirer, a first calculator, and a display image generator. The perspective image generator generates a first perspective image of the target viewed in a first direction, based on three-dimensional volume data of the target. The perspective image acquirer acquires the second perspective image from the detector. The corresponding point acquirer acquires one or more pairs of first and second corresponding points respectively on the first and second perspective images. The first calculator updates the position of the one or more first corresponding point on the first perspective image, based on a difference in position between the first and second perspective images. The display image generator generates a first display image. The first display image may include, but is not limited to, the first and second perspective images, the one or more first corresponding points updated on the first perspective image, and the one or more second corresponding points on the second perspective image. The perspective image generator changes the first direction into a third direction based on the difference in position between the first and second perspective images, and generates an updated one, viewed in the third direction, of the first perspective image. The display system displays the first display image.

In some cases, the system may further include, but is not limited to, a second calculator. The second calculator calculates the difference by calculating a difference in position between the three-dimensional volume data and the target at the time the second perspective image is captured before the second perspective image is acquired by the perspective image acquirer, based on the one or more first and second corresponding points of the first and second perspective images.

In some cases, the corresponding point acquirer acquires one or more pairs of third and fourth corresponding points respectively on the first and second perspective images. The second calculator updates the difference in position between the first and second perspective images, based on the one or more pairs of first and second corresponding points and the one or more pairs of third and fourth corresponding points. The first calculator updates the one or more first and third corresponding points, based on the difference updated lastly in position between the first and second perspective images. The display image generator generates an updated one of the first display image, the updated one includes the lastly updated one of the first display image including the first perspective image and the one or more first and third corresponding points, which are updated lastly, and the second perspective image.

In some cases, the second calculator updates the difference, based on one or more undeleted pairs of the first and second corresponding points acquired, when any corresponding points have been deleted.

In some cases, the corresponding point acquirer determines whether a designated corresponding point on one of the first and second perspective images is a modified corresponding point to which the existent one of the one or more first and second corresponding points or an additional corresponding point to be added to the existent ones of the one or more first and second corresponding points. The corresponding point acquirer deletes a closest existent one, to the designated corresponding point, of the one or more first and second corresponding points in a case that the corresponding point acquirer determines that the designated corresponding point is the modified corresponding point.

In some cases, the image processor may further include, but is not limited to, a corresponding point modifier that calculates a similarity between first and second partial images. The first partial image includes the first corresponding point which position has been last updated by the first calculator. The second partial image includes the second corresponding point which is paired with that first corresponding point. The corresponding point modifier detects a region having a highest similarity to the second partial image from the first perspective image, if the similarity calculated is smaller than a predetermined reference value. The corresponding point modifier modifies the position of the first corresponding point based on the region detected.

In some cases, the display image generator modifies, based on the difference, an epipolar line on the first perspective image. The epipolar line is associated with the one or more first corresponding points.

In some cases, the perspective image generator changes the third direction into a fourth direction based on the difference in position between the updated one, viewed in the third direction, of the first perspective image and the second perspective image. The perspective image generator generates a further updated one, viewed in the fourth direction, of the first perspective image.

According to still other embodiments, an image processing method may include, but is not limited to, the following processes. A first perspective image of a target viewed in a first direction is generated based on three-dimensional volume data of the target. A second perspective image of the target viewed in a second direction is acquired. One or more pairs of first and second corresponding points respectively on the first and second perspective images are acquired. The position of the one or more first corresponding points on the first perspective image is updated based on a difference in position between the first and second perspective images. A first display image is generated. The first display image includes the first and second perspective images, the one or more first corresponding points updated on the first perspective image, and the one or more second corresponding points on the second perspective image. The first direction is changed into a third direction based on the difference in position between the first and second perspective images. An updated one, viewed in the third direction, of the first perspective image is generated.

In some cases, the image processing method may further include, but is not limited to, the following processes. The difference is calculated by calculating a difference in position between the three-dimensional volume data and the target at the time the second perspective image is captured before the second perspective image is acquired, based on the one or more first and second corresponding points of the first and second perspective images. One or more pairs of third and fourth corresponding points respectively on the first and second perspective images are acquired. The difference in position between the first and second perspective images is updated based on the one or more pairs of first and second corresponding points and the one or more pairs of third and fourth corresponding points. The position of the one or more first and third corresponding points is updated based on the difference updated lastly in position between the first and second perspective images. An updated one of the first display image is generated. The updated one includes the first perspective image and the one or more first and third corresponding points, which are updated lastly, and the second perspective image.

According to furthermore embodiments, an image processor may further include, but is not limited to, a processor, and a memory that stores processor-executable instructions that, when executed by the processor, cause the processor to perform the following acts or operations. The processor calculates a difference in position between first and second perspective images. The first perspective image is of a target viewed in a first direction, from three-dimensional volume data of the target. The second perspective image is of the target viewed in a second direction. The processor updates the position of one or more first corresponding points on the first perspective image, based on the difference. The processor changes the first direction into a third direction based on the difference in position between the first and second perspective images. The processor generates an updated one, viewed in the third direction, of the first perspective image.

First Embodiment

Hereinafter, an image processor, a treatment system, and an image processing method according to a first embodiment will be described with reference to drawings. FIG. 1 is a block diagram illustrating a treatment system 10 according to the first embodiment. The treatment system 10 may include, but is not limited to, an image processor 100, a display system 200, and a radiographic imaging apparatus 400. The treatment system 10 may further include, but is not limited to, a planning apparatus 300, a treatment apparatus 500, and a bed 600.

The image processor 100 detects the difference in position of an object A to be treated (hereinafter, "target A"), such as a patient, based on images taken by the radiographic imaging apparatus 400 at the time of planning a treatment (hereinafter, "planning time") and at the time of actually performing the treatment (hereinafter, "treatment time"). The display system 200 displays images taken at the planning time and at the treatment time and receives inputs from a user or an operator, such as a surgeon or a medical doctor. The planning apparatus 300 designate a portion of the target A to be subject to the treatment, based on information concerning the target A obtained before the treatment is performed. The radiographic imaging apparatus 400 captures an image of the target A at the treatment time. The treatment apparatus 500 is used for a treatment on the portion of the target A designated by the planning apparatus 300. The bed 600 shifts, at the treatment time, the target A based on the positional difference detected by the image processor 100 while maintaining a predetermined posture of the target A.

The planning apparatus 300 makes a treatment plan based on an input received through operations by a user, and information, such as images of the inside of the target A which is to be subject to a radiotherapy, a proton therapy, a particle radiotherapy. Images are data captured using a radiographic imaging apparatus that captures an image of the inside of the target A. The radiographic imaging apparatus may be, but is not limited to, an X-ray imaging apparatus, a computed tomography (CT) apparatus, a magnetic resonance imaging (MRI) apparatus, a positron emission tomography (PET) apparatus, a single photon emission computed tomography (SPECT) apparatus, and the like. The images may be either two-dimensional or three-dimensional. In the first embodiment, descriptions are given with respect to a case of using images collected by an X-ray CT apparatus at the planning time.

The planning apparatus 300 may include, but is not limited to, a database 310, a display 320, an operation device 330, and a controller 340. The database 310 stores image data of the target A. The stored image data of the target A may be voxel data itself captured by capturing the image of the target A. The stored image data of the target A may also be voxel data as raw data captured by subjecting projected data to a correction process, such as logarithmic conversion, offset correction, sensitivity correction, beam hardening correction, or scattered radiation correction. The stored image data of the target A may also be two-dimensional image data reconstructed from the voxel data. Descriptions are given in the present embodiment with respect to a case where the database 310 stores voxel data.

The display 320 displays perspective images under the control of the controller 340. Descriptions are given in the present embodiment with respect to a case where a perspective image to be used is a perspective image of the target A viewed in a predetermined direction, which is reconstructed from the voxel data stored in the database 310, that is, a digitally reconstructed radiograph (DRR). It is preferable that the type of the perspective image displayed by the display 320 corresponds to that of an image captured by the radiographic imaging apparatus 400 that will be explained later. This is because use of mutually-associated images enhances precision of the positioning process and makes user input more convenient. Since the case where the radiographic imaging apparatus 400 is an X-ray imaging apparatus is described in the present embodiment, it is preferable that the display 320 displays a DRR image resulting from simulating an image captured by the X-ray imaging apparatus.

The operation device 330 receives an input through operations by a user and supplies information associated with the operations by the user to the controller 340. The controller 340 controls each unit included in the planning apparatus 300 based on the information associated with the operations received by the operation device 330. The controller 340 is an information processing device that includes, for example, a central processing unit (CPU), and performs a process based on a particular program. The controller 340 has the database 310 store information indicating a portion of the target A to be subject to a treatment based on a reconstructed image and information associated with the input received through the operations by the user.

The radiographic imaging apparatus 400 may be, but are not limited to, an X-ray imaging apparatus, a CT apparatus, an MRI apparatus, and the like. The radiographic imaging apparatus 400 is an apparatus that captures an image of the target A. In the first embodiment, a case where the radiographic imaging apparatus 400 is an X-ray imaging apparatus is described. The radiographic imaging apparatus 400 may include, but is not limited to, a controller 410 and first and second image captures. The first image capture includes a first ray irradiator 420 and a first ray detector 440. The second image capture includes a second ray irradiator 430 and a second ray detector 450.

The first ray detector 440 detects an X-ray irradiated from the first ray irradiator 420 and penetrating the target A. The first ray detector 440 makes or generates a perspective image of the target A based on the detected X-ray. The first ray detector 440 may be, but is not limited to, a flat panel detector (FPD) that receives the X-ray penetrating the target A and converts the received X-ray into a digital signal. Based on the digital signal, the first ray detector 440 generates a perspective image of the target A.

The second ray detector 450 detects an X-ray irradiated from the second ray irradiator 430 and penetrating the target A. The second ray detector 450 makes or generates a perspective image of the target A based on the detected X-ray. Similar to the first ray detector 440, the second ray detector 450 includes a flat panel detector (FPD) that receives the X-ray penetrating the target A and converts the received X-ray into a digital signal. Based on the digital signal, the second ray detector 450 generates a perspective image of the target A.

Here, the perspective direction in which the first ray detector 440 views the target A differs from that in which the second ray detector 450 views the target A. For example, the first ray irradiator 420, the second ray irradiator 430, the first ray detector 440, and the second ray detector 450 are disposed so that an image capturing surface for the FPD included in the first ray detector 440 is vertical to an image capturing surface for the FPD included in the second ray detector 450. Here, each of the first and second ray detectors 440 and 450 may include an image intensifier (I.I.), in lieu of the FPD.

The controller 410 controls each unit of the radiographic imaging apparatus 400. The controller 410 is an information processing device that includes, for example, a CPU, and performs a process based on a particular program. The controller 410 supplies the image processor 100 with perspective images of the target A generated by the first and second ray detectors 440 and 450.

The image processor 100 supplies the display system 200 with image data indicating an image generated from the voxel data stored by the database 310 of the planning apparatus 300 and the perspective image received from the radiographic imaging apparatus 400. Additionally, the image processor 100 calculates a difference D in position of the target A between at the planning time and at the treatment time, based on the image generated from the voxel data, the image received from the radiographic imaging apparatus 400, and the information received from the display system 200 and concerning the input received through the operations by the user. The image processor 100 supplies the bed 600 with positioning information indicating the calculated difference D. The details of image processing, or configuration of the image processor 100 will be described.

The display system 200 may include, but is not limited to, a display 210 and an operation device 220. The display 210 receives image data from the image processor 100. The image data may include, but is not limited to, an image generated based on voxel data, and an image captured by the radiographic imaging apparatus 400. The display 210 displays the image indicated by the received image data.

The operation device 220 receives an input through operations by the user and supplies the image processor 100 with information associated with the input received through the operations. The operation device 220 receives an input through operations which designates a point on the image displayed on the display 210 and supplies information concerning a coordinate of the designated point to the image processor 100. The operation device 220 may include, for example, a pointing device such as a keyboard or a mouse, a touch panel, and the like. When the operation device 220 is a touch panel, the operation device 220 may be integrated with the display 210.

The treatment apparatus 500 is an apparatus to be used for subjecting the target A to radiotherapy, a proton therapy, or a particle radiotherapy. The treatment apparatus 500 may include, but is not limited to, a controller 510 and multiple ray irradiators 520. The controller 510 controls each unit of the treatment apparatus 500. The controller 510 is a control processing device that includes a CPU, and performs a process based on a particular program. The controller 510 makes the ray irradiators 520 operable after detecting that the bed 600 shifts the target A based on the difference D detected by the image processor 100. Each of the ray irradiators 520 irradiates, after being made operable, a radio beam, a proton beam, or a particle beam toward the target A based on control by the user. The ray irradiators 520 are disposed such that the radio beams, the proton beams, or the particle beams irradiated from the ray irradiators 520 intersect at one point (isocenter).

The bed 600 may include, but is not limited to, a stage or a chair to place the target A thereon. The bed 600 moves the bed or the chair to place the target A based on the positioning information received from the image processor 100. Thus, the portion of the target A predetermined at the planning time is aligned on the isocenter.

Figure 2:
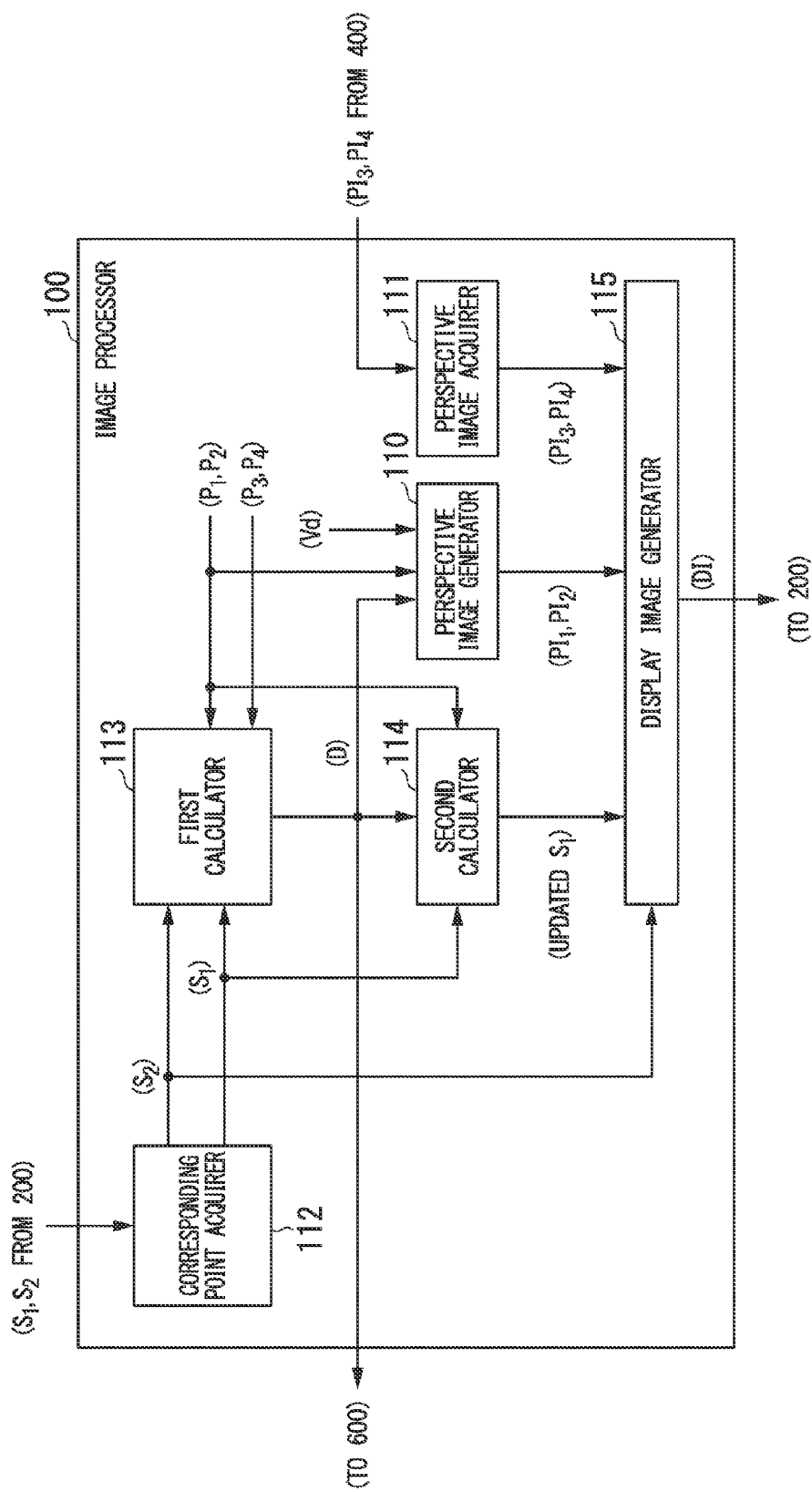
FIG. 2 is a block diagram illustrating an example of an image processor according to the first embodiment.

FIG. 2 is a block diagram illustrating an example of the image processor 100 according to the first embodiment. As shown in FIG. 2, the image processor 100 may include, but is not limited to, a perspective image generator 110, a perspective image acquirer 111, a corresponding point acquirer 112, a first calculator 113, a second calculator 114, and a display image generator 115. In the image processor 100 and the treatment system 10 of the first embodiment, the isocenter of the treatment apparatus 500 is set to be an original point of a world coordinate system used for the positioning process. Additionally, the world coordinate system with the isocenter set to the original point is used as a three-dimensional coordinate to be used in the image processor 100 and the treatment system 10. The isocenter is the point of intersection among the beams irradiated from the ray irradiators 520.

The perspective image generator 110 generates first and second perspective images $IP_1$ and $IP_2$ based on three-dimensional volume data Vd, first and second parameters $C_1$ and $C_2$, and the difference D of the target A. The three-dimensional volume data Vd is voxel data stored by the database 310 of the planning apparatus 300.

The first parameter $C_1$ includes information concerning the posture of a virtual camera at the time the first perspective image $PI_1$ is generated, and information concerning conversion of the three-dimensional coordinate into an image coordinate system which is for the first perspective image $PI_1$. The first parameter $C_1$ include at least a camera parameter (external and internal parameters) of the virtual camera at the time three-dimensional volume data Vd of the target A is virtually captured.

The second parameter $C_2$ includes information concerning the posture of a virtual camera at the time the second perspective image $PI_2$ is generated, and information concerning conversion of the three-dimensional coordinate into an image coordinate system for the second perspective image $PI_2$. Similar to the first parameter $C_1$, examples of the second parameter $C_2$ include a camera parameter of the virtual camera.

The first perspective image $PI_1$ is a DRR image constructed based on, for example, the three-dimensional volume data Vd and the first parameter $C_1$. Similarly, the second perspective image $PI_2$ is a DRR image constructed based on, for example, the three-dimensional volume data Vd and the second parameter $C_2$. The difference D of the target A is a value indicating the difference in position of the target A between at the time the three-dimensional volume data is captured and at the time the treatment is performed. The difference D of the target A is output from the first calculator 113 and is input to the perspective image generator 110.

The perspective image generator 110 shifts the three-dimensional volume data Vd to the position at the treatment time based on the difference D of the target A, and then generates the first and second perspective images $PI_1$ and $PI_2$ using the first and second parameters $C_1$ and $C_2$.

The perspective image acquirer 111 receives a pair of perspective images of the target A generated by the radiographic imaging apparatus 400. Hereinafter, between the pair of perspective images, the perspective image generated by the first ray detector 440 is referred to as a third perspective image $PI_3$, and the perspective image generated by the second ray detector 450 is referred to as a fourth perspective image $PI_4$. The camera parameter of the first ray detector 440 is referred to as a third parameter $C_3$. The camera parameter of the second ray detector 450 is referred to as a fourth parameter $C_4$. The same type of parameters is used as the first and third parameters $C_1$ and $C_3$. The same type of parameters is used as the second and fourth parameters $C_2$ and $C_4$.

The corresponding point acquirer 112 receives from the operation device 220 of the display system 200, at least one group of four corresponding points on the respective first to fourth perspective images $PI_1$ to $PI_4$. The corresponding points on the first and second perspective images $PI_1$ and $PI_2$ are defined as a first group of points $S_1$. The corresponding points on the third and fourth perspective images $PI_3$ and $PI_4$ are defined as a second group of points $S_2$.

The first calculator 113 calculates the difference D of the target A based on the first and second groups of points $S_1$ and $S_2$, and the first to fourth parameters $C_1$ to $C_4$. The second calculator 114 performs an update process of shifting, based on the first group of points $S_1$, the first and second parameters $C_1$ and $C_2$, and the difference D of the target A, the coordinate of each corresponding point of the first group of points $S_1$ which is on the first or second perspective image to a position approximating to the position of the associated corresponding point of the second group of points $S_2$ which is on the third or fourth perspective images $IP_3$ and $IP_4$.

The display image generator 115 generates a display image DI to be displayed by the display system 200, using the first to fourth perspective images $PI_1$ to $PI_4$, and the first and second groups of points $S_1$ and $S_2$. The display image generator 115 supplies the display system 200 with image data indicating the generated display image DI. For example, on the display image DI, the first and third perspective images $PI_1$ and $PI_3$ are arranged adjacent to each other, and the second and fourth perspective images $PI_2$ and $PI_4$ are arranged adjacent to each other, thereby enabling easy comparison of the images captured at the planning time and at the treatment time. Here, the corresponding points designated by the user (first and second groups of points $S_1$ and $S_2$) may be superimposed on the first to fourth perspective images $PI_1$ to $PI_4$.

Figure 3:
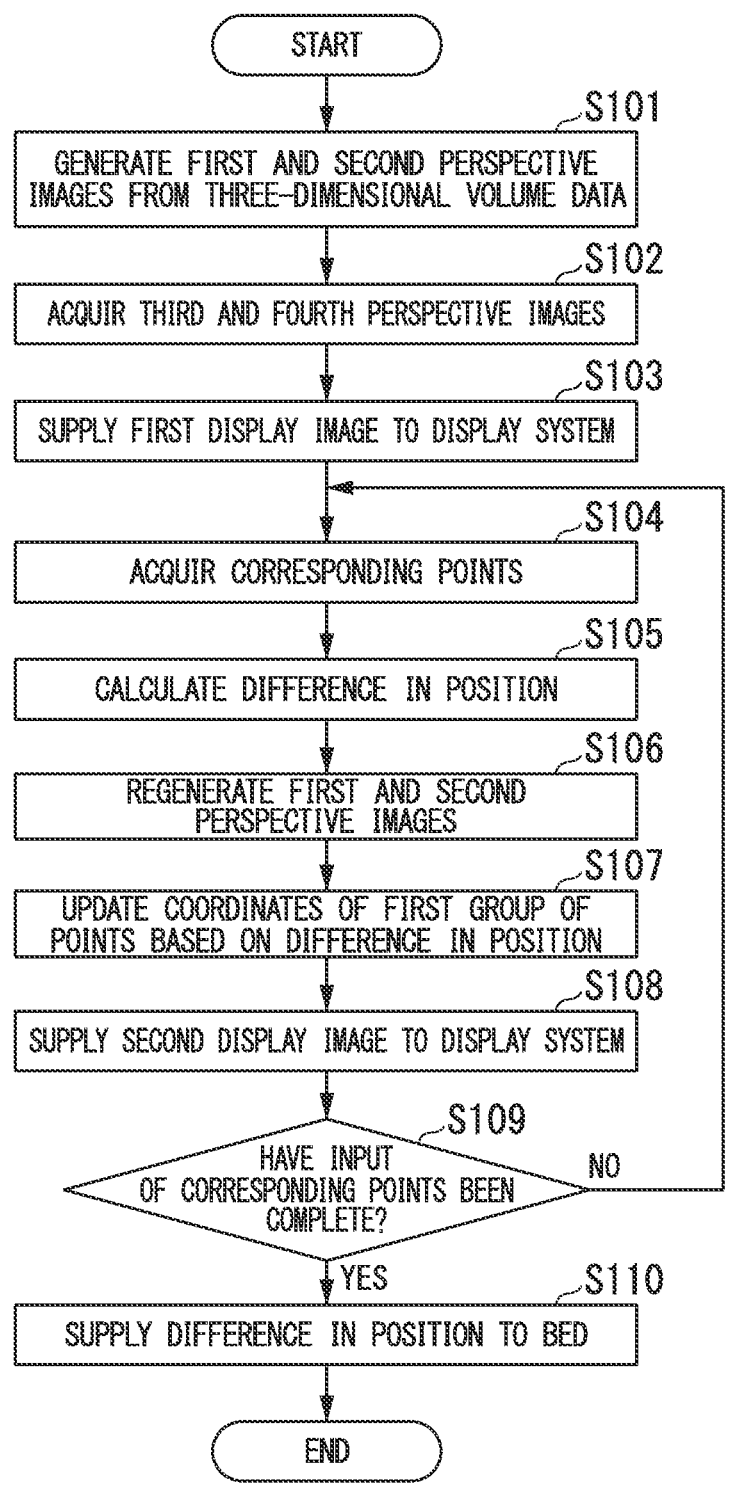
FIG. 3 is a flowchart illustrating a positioning process to be performed by the image processor according to the first embodiment.

FIG. 3 is a flowchart illustrating a positioning process to be performed by the image processor 100 according to the first embodiment. When the image processor 100 initiates the positioning process, the perspective image generator 110 generates the first and second perspective images $PI_1$ and $PI_2$ based on the three-dimensional volume data Vd, the first and second parameters $C_1$ and $C_2$, and the difference D of the target A (step S101).

The perspective image acquirer 111 acquires the third and fourth perspective images $PI_3$ and $PI_4$ captured by the radiographic imaging apparatus 400 capturing images of the target A (step S102).

The display image generator 115 generates a first display image $DI_1$ including the first and second perspective images $PI_1$ and $PI_2$ generated in step S101 and the third and fourth perspective images $PI_3$ and $PI_4$ captured in step S102. The display image generator 115 supplies the display system 200 with the generated first display image $DI_1$, and has the display system 200 display the first display image $DI_1$, thereby having the user compare the first to fourth perspective images $PI_1$ to $PI_4$ (step S103).

The corresponding point acquirer 112 acquires at least one group of four corresponding points (first and second groups of points $S_1$ and $S_2$) designated by the user respectively on the first to fourth perspective images $PI_1$ to $PI_4$ displayed by the display system 200 (step S104). The first calculator 113 calculates the difference D of the target A based on the corresponding points captured in step S104 and the first to fourth parameters $C_1$ to $C_4$ (step S105).

The perspective image generator 110 regenerates first and second perspective images $PI_1'$ and $PI_2'$ based on the difference D of the target A calculated in step S105, the three-dimensional volume data Vd, and the first and second parameters $C_1$ and $C_2$ (step S106). The second calculator 114 updates the coordinates of the first group of points $S_1$ using the difference D of the target A calculated in step S105 and the first and second parameters $C_1$ and $C_2$ (step S107).

The display image generator 115 generates a second display image $DI_2$ including the first and second perspective images $PI_1'$ and $PI_2'$ regenerated in step S106, the first group of points $S_1$ updated in step S107, the third and fourth perspective images $PI_3$ and $PI_4$ captured in step S102, and the second group of points $S_2$. The display image generator 115 supplies the display system 200 with image data indicating the generated second display image $DI_2$, and has the display system 200 display the second display image $DI_2$, thereby having the user compare the first to fourth perspective images $PI_1'$, $PI_2'$, $PI_3$, and $PI_4$, and the first and second groups of points $S_1$ and $S_2$ (step S108).

The corresponding point acquirer 112 determines whether or not an operation by the user, which indicates that input of corresponding points has been complete, is received via the operation device 220 (step S109).

If the input of corresponding points has not been complete (step S109: NO), the corresponding point acquirer 112 returns the processing to step S104.

If the input of corresponding points has been complete (step S109: YES), on the other hand, the first calculator 113 supplies the difference D of the target A to the bed 600 and has the bed 600 perform a positioning process (step S110), and then terminates the positioning process.

Figure 4:
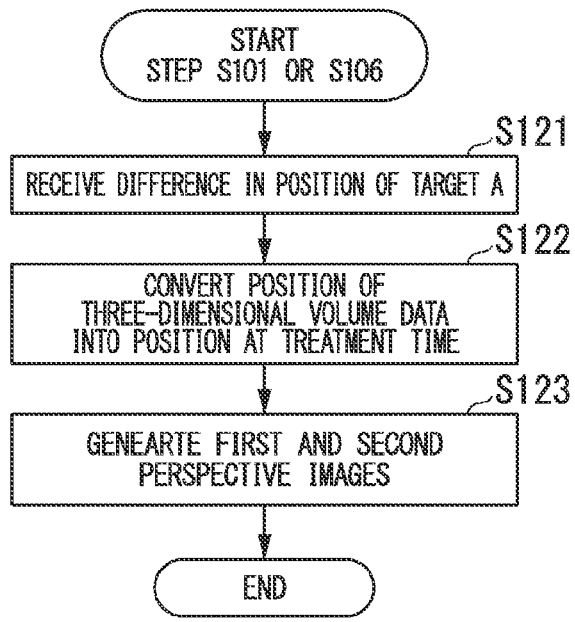
FIG. 4 is a flowchart illustrating processes included in the positioning process to be performed by a perspective image generator according to the first embodiment.

Hereinafter, the above process in each step will be described in detail. FIG. 4 is a flowchart illustrating the processes in steps S101 and S106 to be performed by the perspective image generator 110 in the positioning process of the first embodiment. The perspective image generator 110 receives the difference D of the target A from the first calculator 113 (step S121). In step 101, the difference D of the target A has not yet been calculated by the first calculator 113. For this reason, in step S101, a default value predetermined or set by the user may be used as the difference D of the target A.

The difference D of the target A is a value based on rotation and translation of the target A performed to shift the position of the target A at the treatment time to the position of the target A at the time the three-dimensional volume data Vd is captured. For example, the difference D of the target A can be expressed as a 3×3 rotation matrix R and a translation vector t, as shown in the following Expressions (1-1) and (1-2).

$$R = \begin{bmatrix} r_1 & r_2 & r_3 \\ r_4 & r_5 & r_6 \\ r_7 & r_8 & r_9 \end{bmatrix} \quad (1\text{-}1)$$

$$t = \begin{bmatrix} t_1 \\ t_2 \\ t_3 \end{bmatrix} \quad (1\text{-}2)$$

Additionally, as the rotation-based value, ($\Delta R_x$, $\Delta R_y$, $\Delta R_z$), which are the rotation angles around the X-axis, the Y-axis, and the Z-axis of the world coordinate system converted from the rotation matrix R, may be used, in lieu of the rotation matrix R. Assuming that rotation is made around the X-axis, the Y-axis, and the Z-axis in this order, the conversion from the rotation matrix R into the rotation angles ($\Delta R_x$, $\Delta R_y$, $\Delta R_z$) can be made by the following Expression (2).

$$\begin{cases} \Delta R_x = \sin^{-1}\left(r_4 / \sqrt{1-r_7^2}\right) \\ \Delta R_y = \sin^{-1}(-r_7) \\ \Delta R_z = \sin^{-1}\left(r_8 / \sqrt{1-r_7^2}\right) \end{cases} \quad (2)$$

The perspective image generator 110 converts the position of the three-dimensional volume data Vd of the target A into the position of the target A at the treatment time based on the rotation matrix R and the translation vector t which indicate the difference D of the target A (step S122). Here, conversion from a position X into a position Y can be made by the following Expression (3) using the rotation matrix R and the translation vector t, where the position X represents the position of the target A at the treatment time, and the position Y represents the position of the three-dimensional volume data Vd.

$$Y = RX + t \quad (3)$$

The position X is obtained from Expression (3), thereby making it possible to shift the position Y of the three-dimensional volume data to a position Y' which is closer to the position X of the target A at the treatment time. The position Y' is obtained from the following Expression (4). When the rotation matrix R and the translation vector t are accurate, the position X matches the position Y'.

$$Y' = R^{-1}(Y - t) \quad (4)$$

The perspective image generator 110 generates a first perspective image $PI_1$ by having a first virtual camera $VC_1$ set with the first parameter capture an image of the shifted three-dimensional volume data Vd. Additionally, the perspective image generator 110 generates a second perspective image $PI_2$ by having a second virtual camera $VC_2$ set with the second parameter capture an image of the shifted three-dimensional volume data Vd (step S123).

Thus, the perspective image generator 110 generates the first and second perspective images $PI_1$ and $PI_2$.

Hereinafter, procedure for the first calculator 113 to calculate the difference D of the target A in step S105 is explained. The difference D calculated by the first calculator 113 is indicated by the rotation matrix R and the translation vector t, as explained above. Regarding the n-th group of corresponding points (n≥1) among the N groups of corresponding points captured in step S104, a coordinate of a first point of the n-th group of corresponding points, which is on the first perspective image $PI_1$ is represented as $(u_n^{(1)}, v_n^{(1)})$. A coordinate of a second point of the n-th group of corresponding points, which is on the second perspective image $PI_2$ and corresponds to the first point $(u_n^{(1)}, v_n^{(1)})$, is represented as $(u_n^{(2)}, v_n^{(2)})$. A coordinate of a third point of the n-th group of corresponding points, which is on the third perspective image $PI_3$ and corresponds to the first point $(u_n^{(1)}, v_n^{(1)})$, is represented as $(u_n^{(3)}, v_n^{(3)})$. A coordinate of a fourth point of the n-th group of corresponding points, which is on the fourth perspective image $PI_4$ and corresponds to the first point $(u_n^{(1)}, v_n^{(1)})$ is represented as $(u_n^{(4)}, v_n^{(4)})$. Additionally, the first group of points $S_1$ is represented as $\{(u_n^{(3)}, v_n^{(3)}), (u_n^{(4)}, v_n^{(4)})\}$ (n=1, ..., N). The second group of points $S_2$ is represented as $\{(u_n^{(3)}, v_n^{(3)}), (u_n^{(4)}, v_n^{(4)})\}$ (n=1, ..., N).

The first calculator 113 selects a method of calculating the difference D in accordance with the number of groups of corresponding points N captured by the corresponding point acquirer 112. There are four different methods of calculating the difference D. The first method is used when N=1. The second method is used when N=2. The third method is used when N=3. The fourth method is used when N≥4. Hereinafter, the four methods of calculating the difference D are sequentially described.

(First Calculating Method for N=1)

A first point of the first group of points $S_1$, which is on the first perspective image $PI_1$, is represented as $(u^{(1)}, v^{(1)})$. A second point of the first group of points $S_1$, which is on the second perspective image $PI_2$, is represented as $(u^{(2)}, v^{(2)})$. A third point of the second group of points $S_2$, which is on the third perspective image $PI_3$, is represented as $(u^{(3)}, v^{(3)})$. A fourth point of the second group of points $S_2$, which is on the fourth perspective image $PI_4$, is represented as $(u^{(4)}, v^{(4)})$. Additionally, the first to fourth parameters $C_1$ to $C_4$ are defined by the following Expression (5).

$$C_j = \begin{bmatrix} c_{11}^{(j)} & c_{12}^{(j)} & c_{13}^{(j)} & c_{14}^{(j)} \\ c_{21}^{(j)} & c_{22}^{(j)} & c_{23}^{(j)} & c_{24}^{(j)} \\ c_{31}^{(j)} & c_{32}^{(j)} & c_{33}^{(j)} & c_{34}^{(j)} \end{bmatrix} \tag{5}$$

In Expression (5), j (j=1, 2, 3, 4) represents the parameter number. The three-dimensional coordinate $Y=(y_1, y_2, y_3)$ is calculated from the following Expression (6) using the first point $(u^{(1)}, v^{(1)})$ on the first perspective image $PI_1$, the second point $(u^{(2)}, v^{(2)})$ on the second perspective image $PI_2$, and the first and second parameters $C_1$ and $C_2$.

$$\begin{bmatrix} y_1 \\ y_2 \\ y_3 \end{bmatrix} = \begin{bmatrix} c_{31}^{(1)}u^{(1)} - c_{11}^{(1)} & c_{32}^{(1)}u^{(1)} - c_{12}^{(1)} & c_{33}^{(1)}u^{(1)} - c_{13}^{(1)} \\ c_{31}^{(1)}v^{(1)} - c_{21}^{(1)} & c_{32}^{(1)}v^{(1)} - c_{22}^{(1)} & c_{33}^{(1)}v^{(1)} - c_{23}^{(1)} \\ c_{31}^{(2)}u^{(2)} - c_{11}^{(2)} & c_{32}^{(2)}u^{(2)} - c_{12}^{(2)} & c_{33}^{(2)}u^{(2)} - c_{13}^{(2)} \\ c_{31}^{(2)}v^{(2)} - c_{21}^{(2)} & c_{32}^{(2)}v^{(2)} - c_{22}^{(2)} & c_{33}^{(2)}v^{(2)} - c_{23}^{(2)} \end{bmatrix}^{-1} \begin{bmatrix} c_{14}^{(1)} - c_{34}^{(1)}u^{(1)} \\ c_{24}^{(1)} - c_{34}^{(1)}v^{(1)} \\ c_{14}^{(2)} - c_{34}^{(2)}u^{(2)} \\ c_{24}^{(2)} - c_{34}^{(2)}v^{(2)} \end{bmatrix} \tag{6}$$

Similarly, the three-dimensional coordinate $X=(x_1, x_2, x_3)$ is calculated using the third point $(u^{(3)}, v^{(3)})$ of the second group of points $S_2$ which is on the third perspective image $PI_3$, the fourth point $(u^{(4)}, v^{(4)})$ of the second group of points $S_2$, and the third and fourth parameters $C_3$ and $C_4$. Using the calculated three-dimensional coordinates X and Y, the translation vector t is calculated by the following Expression (7).

$$t = \begin{bmatrix} t_1 \\ t_2 \\ t_3 \end{bmatrix} = \begin{bmatrix} x_1 - y_1 \\ x_2 - y_2 \\ x_3 - y_3 \end{bmatrix} \tag{7}$$

At this time, the rotation matrix R is assumed to be a 3×3 unit matrix.

Thus, when one group of corresponding points is captured, the first calculator 113 calculates the rotation matrix R and the translation vector t by the above first calculating method.

(Second Calculating Method for N=2)

The first calculator 113 calculates two three-dimensional coordinates $Y_1=(y(1)_1, y(1)_2, y(1)_3)$ and $Y_2=(y(2)_1, y(2)_2, y(2)_3)$ from two groups of corresponding points included in the first group of points $S_1$. Additionally, the first calculator 113 calculates two three-dimensional coordinates $X_1=(x(1)_1, x(1)_2, x(1)_3)$ and $X_2=(x(2)_1, x(2)_2, x(2)_3)$ from two groups of corresponding points included in the second group of points $S_2$. Here, calculation of the three-dimensional coordinates is performed in a similar manner as in the case of N=1.

From Expression (3), the three-dimensional coordinates $X_1$ and $Y_1$ meet $Y_1=RX_1+t$, and the three-dimensional coordinates $X_2$ and $Y_2$ meet $Y_2=RX_2+t$. A vector $(Y_2-Y_1)$ extending from the three-dimensional coordinate $Y_1$ to the three-dimensional coordinate $Y_2$ can be obtained by the following Expression (8).

$$Y_2 - Y_1 = RX_2 + t - (RX_1 + t) \tag{8}$$
$$= R(X_2 - X_1)$$

It can be understood from Expression (8) that the relationship between the vector $(Y_2-Y_1)$ extending from the three-dimensional coordinate $Y_1$ to the three-dimensional coordinate $Y_2$ and the vector $(X_2-X_1)$ extending from the three-dimensional coordinate $X_1$ to the three-dimensional coordinate $X_2$ is dependent only on the rotation matrix R. Here, angle θ between vectors a and b can be expressed by the following Expression (9), where the vector a represents the vector $(X_2-X_1)$ extending from the three-dimensional coordinate $X_1$ to the three-dimensional coordinate $X_2$, and a vector b represents vector $(Y_2-Y_1)$ extending from the three-dimensional coordinate $Y_1$ to the three-dimensional coordinate $Y_2$.

$$\theta = \cos^{-1}\left(\frac{a \cdot b}{\|a\|\|b\|}\right) \tag{9}$$

In Expression (9), "a·b" represents a scalar product of the vectors a and b. ‖a‖ represents the magnitude of the vector a, and ‖b‖ represents the magnitude of the vector b. Additionally, a unit vector d in the direction of the axis around which the rotation is made by the angle θ is calculated by the following Expression (10).

$$\begin{cases} c = a \times b \\ d = \begin{bmatrix} d_1 \\ d_2 \\ d_3 \end{bmatrix} = \frac{1}{\sqrt{c_1^2 + c_2^2 + c_3^2}} \begin{bmatrix} c_1 \\ c_2 \\ c_3 \end{bmatrix} \end{cases} \tag{10}$$

In Expression (10), "a×b" represents a cross product of the vectors a and b. The vector d represents a vector obtained by normalizing to 1, the magnitude of the vector c obtained from the cross product a×b. The vector b represents a vector obtained by rotating the vector a by the rotation angle θ around the unit vector d. Therefore, the rotation matrix R is calculated by the following Expression (11) using the Rodrigues's formula.

$$R = \cos\theta I + (1-\cos\theta)dd^T + \sin\theta[d]_\times \tag{11}$$

In Expression (11), I represents a 3×3 unit matrix. $[d]_\times$ is a 3×3 unit matrix expressed by the Expression (12).

$$[d]_\times = \begin{bmatrix} 0 & -d_3 & d_2 \\ d_3 & 0 & -d_1 \\ -d_2 & d_1 & 0 \end{bmatrix} \tag{12}$$

After the rotation matrix R is calculated, the translation vector t is calculated using the following Expression (13) derived from Expression (3).

$$t = Y_n - RX_n \tag{13}$$

In Expression (13), n may be any one of 1 and 2. Additionally, an average of a translation vector calculated when n=1 and a translation vector calculated when n=2 may be set to be the translation vector t.

Thus, when two groups of corresponding points are captured, the first calculator 113 calculates the rotation matrix R and the translation vector t by the above second calculating method.

[Third Calculating Method for N=3]

Figure 5:
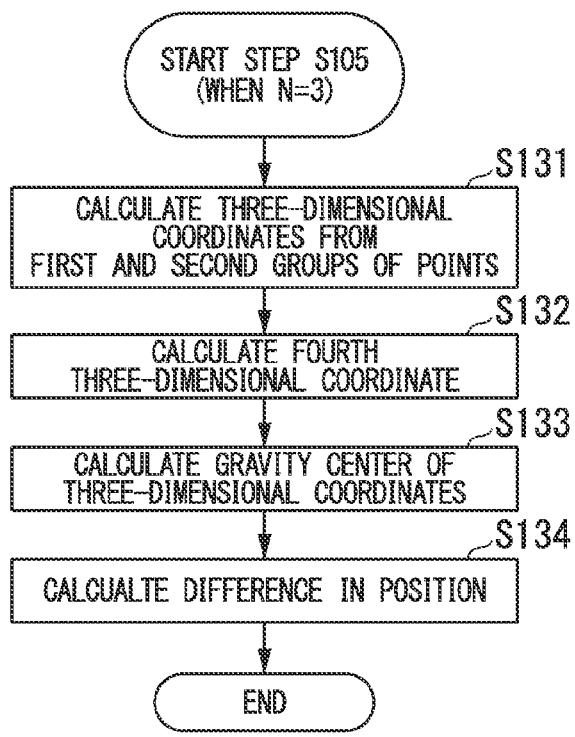
FIG. 5 is a flowchart illustrating procedure for a first calculator to calculate a rotation matrix and a translation vector in a case where there are three groups of corresponding points according to the first embodiment.

FIG. 5 is a flowchart illustrating procedure for the first calculator 113 to calculate the rotation matrix R and the translation vector t when there are three groups of corresponding points in the first embodiment. The first calculator 113 calculates three three-dimensional coordinates $Y_n$ (n=1, 2, 3) respectively from three groups of corresponding points included in the first group of points $S_1$, and calculates three three-dimensional coordinates $X_n$ (n=1, 2, 3) respectively from the three associated groups of the corresponding points included in the second group of points (step S131).

The first calculator 113 calculates the fourth three-dimensional coordinate $X_4$ included in the first group of point $S_1$ using the three-dimensional coordinates $Y_n$ calculated in step S131, and calculates the fourth three-dimensional coordinate $Y_4$ included in the second group of point $S_2$ using the three-dimensional coordinates $X_n$ calculated in step S131 (step S132).

To calculate the fourth three-dimensional coordinate, a gravity center $X_c=(X_1+X_2+X_3)/3$ of the three-dimensional coordinates $X_n$ (n=1, 2, 3) is calculated. Here, a vector extending from the gravity center $X_c$ to the three-dimensional coordinate $X_1$ is represented as a vector e, and a vector extending from the gravity center $X_c$ to the three-dimensional coordinate $X_2$ is represented as a vector f. The fourth three-dimensional coordinate $X_4$ is defined as a three-dimensional coordinate obtained by shifting the gravity center $X_c$ by an arbitrary length l in the direction of a cross product e×f of the vector e and the vector f.

Similarly, a gravity center $Y_c=(Y_1+Y_2+Y_3)/3$ of the three-dimensional coordinates $Y_n$ (n=1, 2, 3) is calculated. Then, the fourth three-dimensional coordinate $Y_4$ is calculated using the gravity center $Y_c$ and the three-dimensional coordinates $Y_1$ and $Y_2$.

The first calculator 113 calculates a gravity center of the first to fourth three-dimensional coordinates $X_1$ to $X_4$ and a gravity center of the first to fourth three-dimensional coordinates $Y_1$ to $Y_4$, using the following Expressions (14-1) and (14-2) (step S133).

$$\overline{X} = \frac{1}{N}\sum_1^N X_n \quad (14\text{-}1)$$

$$\overline{Y} = \frac{1}{N}\sum_1^N Y_n \quad (14\text{-}2)$$

In Expression (14-1), "$\overline{X}$" represents the gravity center of $X_n$ (n=1, 2, 3, 4). In Expression (14-2), "$\overline{Y}$" represents the gravity center of $Y_n$ (n=1, 2, 3, 4).

The first calculator 113 calculates difference D (indicated by the rotation matrix R and the translation vector t) using the three-dimensional coordinates $X_n$ and $Y_n$ (n=1, 2, 3), and the gravity centers $\overline{X}$ and $\overline{Y}$ (step S134).

Specifically, each of the three-dimensional coordinates $X_n$ (n=1, 2, 3) is shifted by subtracting therefrom the gravity center $\overline{X}$ to calculate the three-dimensional coordinates $X_n'=X_n-\overline{X}$. Additionally, each of the three-dimensional coordinates $Y_n$ is shifted by subtracting therefrom the gravity center $\overline{Y}$ to calculate the three-dimensional coordinates $Y_n'=-\overline{Y}$. Then, a matrix X' is defined as X'=$[X_1', X_2', X_3']$, and a matrix Y' is defined as Y'=$[Y_1', Y_2', Y_3']$.

As a result of shifting each of the three-dimensional coordinates by subtracting therefrom the gravity center, the translation vector t is cancelled. For this reason, the relationship between the matrices X' and Y' can be expressed, using the rotation matrix R, by the following Expression (15).

$$Y'=RX' \quad (15)$$

The rotation matrix R meeting Expression (15) can be calculated from Expression (16), using the singular value decomposition (SVD).

$$\begin{cases} U\Sigma V^T = svd(X'Y'^T) \\ R = VU^T \end{cases} \quad (16)$$

In Expression (16), the matrixes U and V are matrixes obtained from the singular value decomposition. Then, the translation vector t is calculated by the following Expression (17), using the rotation matrix R.

$$t=\overline{X}-R\overline{Y} \quad (17)$$

Here, the translation vector t may be calculated using the following Expression (18), in lieu of Expression (17). Alternatively, an average of the translation vectors for n=1, 2, 3, 4 may be set to be the translation vector t.

$$t=X_n-RY_n \quad (18)$$

Thus, in a case where three groups of corresponding points are captured, the first calculator 113 calculates the rotation matrix R and the translation vector t by the above third calculating method.

[Calculating Method for N≥4]

When there are four or more groups of corresponding points, four or more three-dimensional coordinates $Y_n$ are obtained from the first group of points $S_1$, and four or more three-dimensional coordinates $X_n$ are obtained from the second group of points $S_2$. When N≥4, compared with when N=3, a fourth three-dimensional coordinate needs not be calculated. For this reason, step S132 in the procedure shown in FIG. 5 can be omitted. In other words, when four or more groups of corresponding points are received, the first calculator 113 sequentially performs the processes in steps S131, S133, and S134 shown in FIG. 5 on all the N groups of corresponding points, thus calculating the rotation matrix R and the translation vector t.

Then, procedure for the second calculator 114 to update the coordinates of the first group of points $S_1$ in step S107 is described. Among the points included in the first group of points $S_1$, the coordinates of the points on the first perspective image $PI_1$ are represented as $(u(n)^{(1)}, v(n)^{(1)})$, and the coordinates of the points on the second perspective image $PI_2$ are represented as $(u(n)^{(2)}, v(n)^{(2)})$, where n=1, ..., N, and N represents the number of groups of corresponding points.

Figure 6:
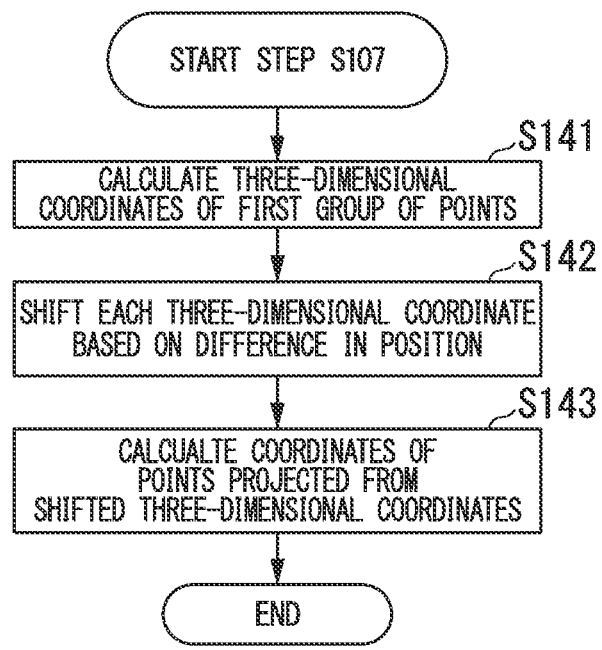
FIG. 6 is a flowchart illustrating procedure for a second calculator to update coordinates of a first group of points according to the first embodiment.

FIG. 6 is a flowchart illustrating procedure for the second calculator 114 to update the coordinates of the first group of points $S_1$ according to the first embodiment. The second calculator 114 calculates three-dimensional coordinates $Y_n$ of the respective points included in the first group of points $S_1$, using Expression (6) (step S141).

The second calculator 114 shifts the three-dimensional coordinate $Y_n$ using the difference D (indicated by the rotation matrix R and the translation vector t) calculated by the first calculator 113, thus calculating a three-dimensional coordinate $\tilde{Y}_n$ (step S142). The three-dimensional coordinates $\tilde{Y}_n$ are positions close to the three-dimensional coordinates $X_n$ of the corresponding points included in the second group of points $S_2$. Here, when the rotation matrix R and the translation vector t are accurate, the three-dimensional coordinates $\tilde{Y}_n$ substantially match the respective three-dimensional coordinates $X_n$.

The three-dimensional coordinates $\tilde{Y}_n$ are calculated by the following Expression (19), using Expression (4) and the difference D (indicated by the rotation matrix R and the translation vector t).

$$\tilde{Y}_n = R^{-1}(Y_n - t) \quad (19)$$

The second calculator 114 calculates updated coordinates $(u'(n)^{(1)}, v'(n)^{(1)})$ on the first perspective image $PI_1$ and updated coordinates $(u'(n)^{(2)}, v'(n)^{(2)})$ on the second perspective image $PI_2$, which are projected from the three-dimensional coordinate $\tilde{Y}_n$ using the first and second parameters $P_1$ and $P_2$ defined by Expression (5) (step S143). The coordinates $(u'(n)^{(1)}, v'(n)^{(1)})$ and $(u'(n)^{(2)}, v'(n)^{(2)})$ of the updated points are calculated using the following Expression (20).

$$\lambda \begin{bmatrix} u'(n)^{(j)} \\ v'(n)^{(j)} \\ 1 \end{bmatrix} = C_j \tilde{Y}_n \quad (20)$$

In Expression (20), $\lambda$ represents the element on the third row of the 3×1 matrix obtained from $C_j \tilde{Y}_n$.

Thus, the second calculator 114 updates the coordinates of the first group of points $S_1$.

In the aforementioned positioning process, the image processor 100 according to the first embodiment calculates the difference D based on the groups of corresponding points input by the user. Based on the calculated difference D, the image processor 100 regenerates the first and second perspective images $PI_1'$ and $PI_2'$ and updates the coordinates of the groups of corresponding points. The image processor 100 has the display system 200 display a display image DI including the regenerated first and second perspective images $PI_1'$ to $PI_4'$, the third and fourth perspective images $PI_3$ and $PI_4$, and the updated corresponding points. While the regeneration and displaying of the first and second perspective images $PI_1'$ and $PI_2'$, the user can input corresponding points on the perspective images at the planning time (first and second perspective images $PI_1'$ and $PI_2'$) and the perspective images at the treatment time (third and fourth perspective images $PI_3$ and $PI_4$). In a case that there is a difference in posture of the target A between at the planning time and at the treatment time, it is possible to make the perspective images at the planning time more similar to the perspective images at the treatment time, thereby making it easier for the user or operator to designate the corresponding points. In another case that there is another difference in position of the target A between at the planning time and A at the time an X-ray photography is taken, it is also possible to make the perspective images at the planning time more similar to the perspective images at the time the X-ray photography is taken, thereby making it easier for the user or operator to designate the corresponding points. Consequently, it is possible to improve the precision of the positioning process, thereby enabling more precise treatment.

Figure 7:
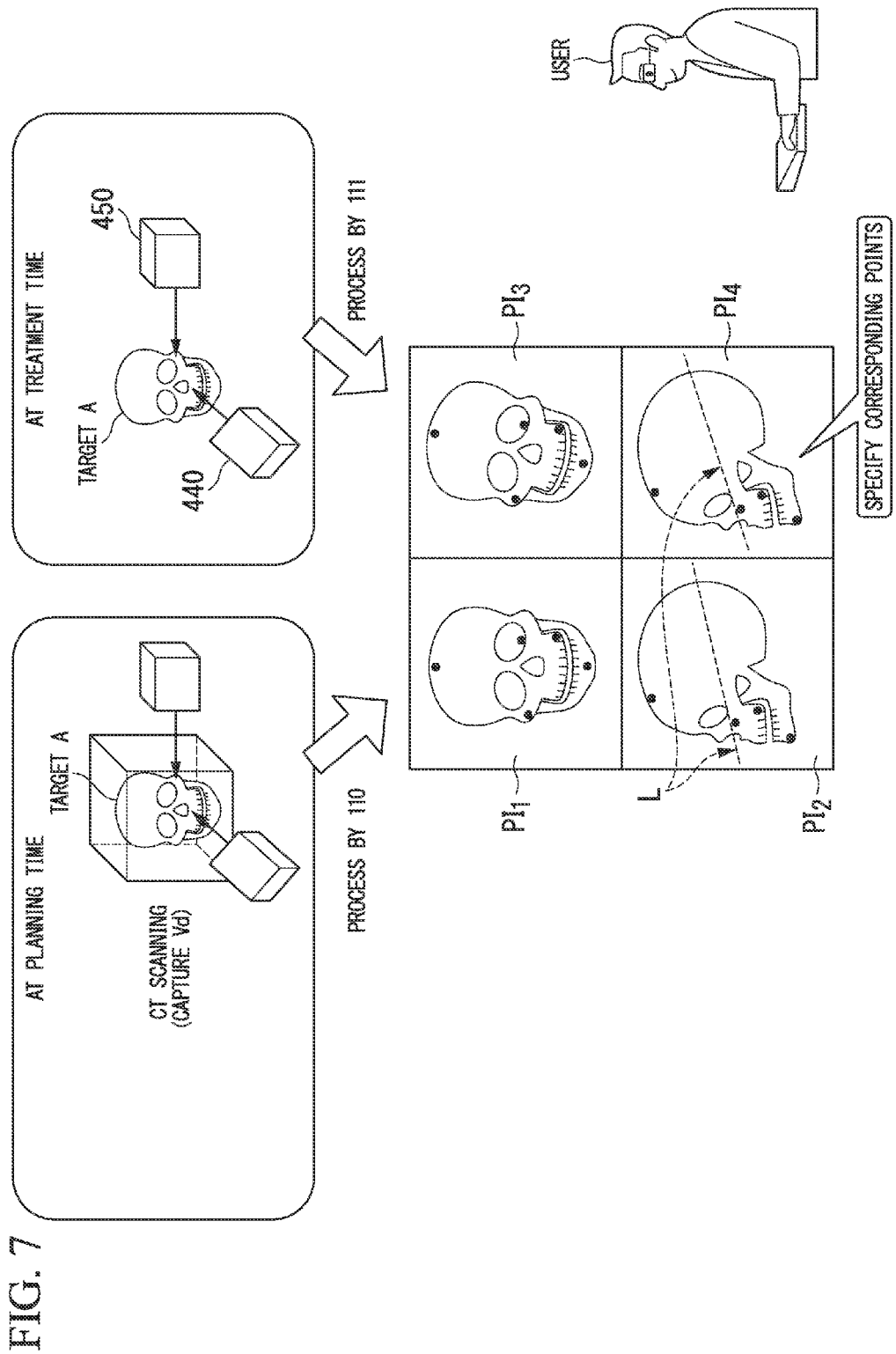
FIG. 7 illustrates outline of the positioning process to be performed by the image processor according to the first embodiment.

FIG. 7 illustrates outline of the positioning process performed by the image processor 100 according to the first embodiment. The image processor 100 generates first and second perspective images $PI_1$ and $PI_2$ based on the three-dimensional volume data Vd stored in the database 310 of the planning apparatus 310. The image processor 100 captures third and fourth perspective images $PI_3$ and $PI_4$ captured by the radiographic imaging apparatus 400 at the treatment time. The image processor 100 supplies the display system 200 with a display image DI including the generated first and second perspective images $PI_1$ and $PI_2$ and the captured third and fourth perspective images $PI_3$ and $PI_4$, thus presenting the display image DI to the user. The image processor 100 receives, through operations by the user, an input of information indicating at least one group of corresponding points indicating the four corresponding portions respectively on the first to fourth perspective images $PI_1$ to $PI_4$. Then, the image processor 100 calculates a difference D indicating the difference in position of the target A between at the planning time and at the treatment time. Based on the difference D, the image processor 100 shifts the three-dimensional volume data Vd and then regenerates first and second perspective images $PI_1'$ and $PI_2'$.

Figure 8:
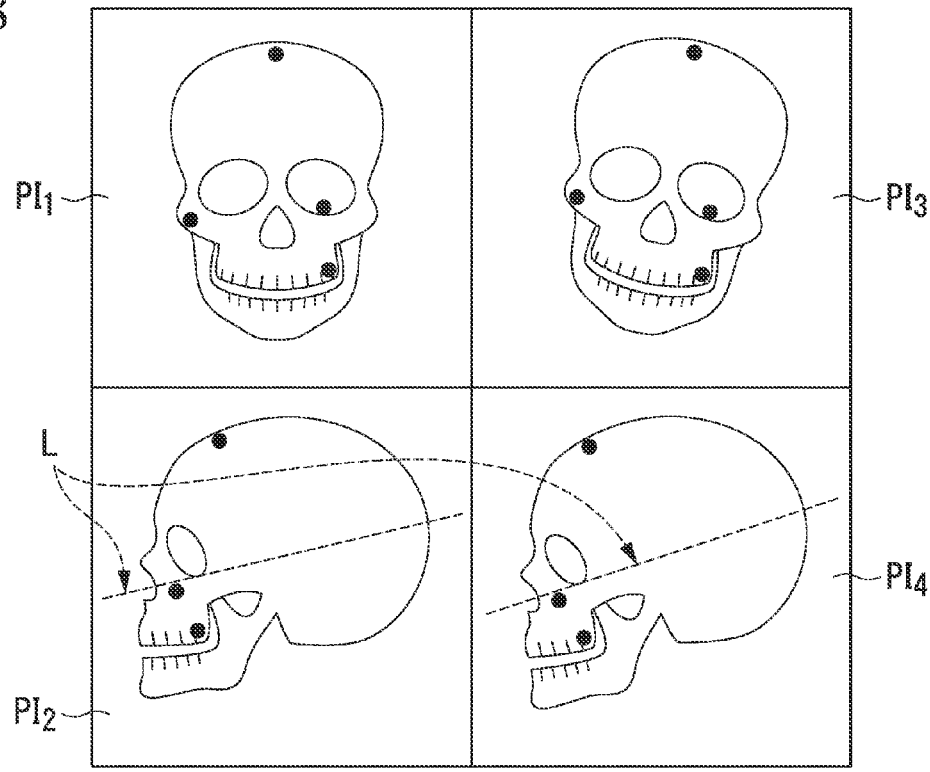
FIG. 8 illustrates an example of regeneration of first and second perspective images to be performed by the image processor according to the first embodiment.
Figure 9:
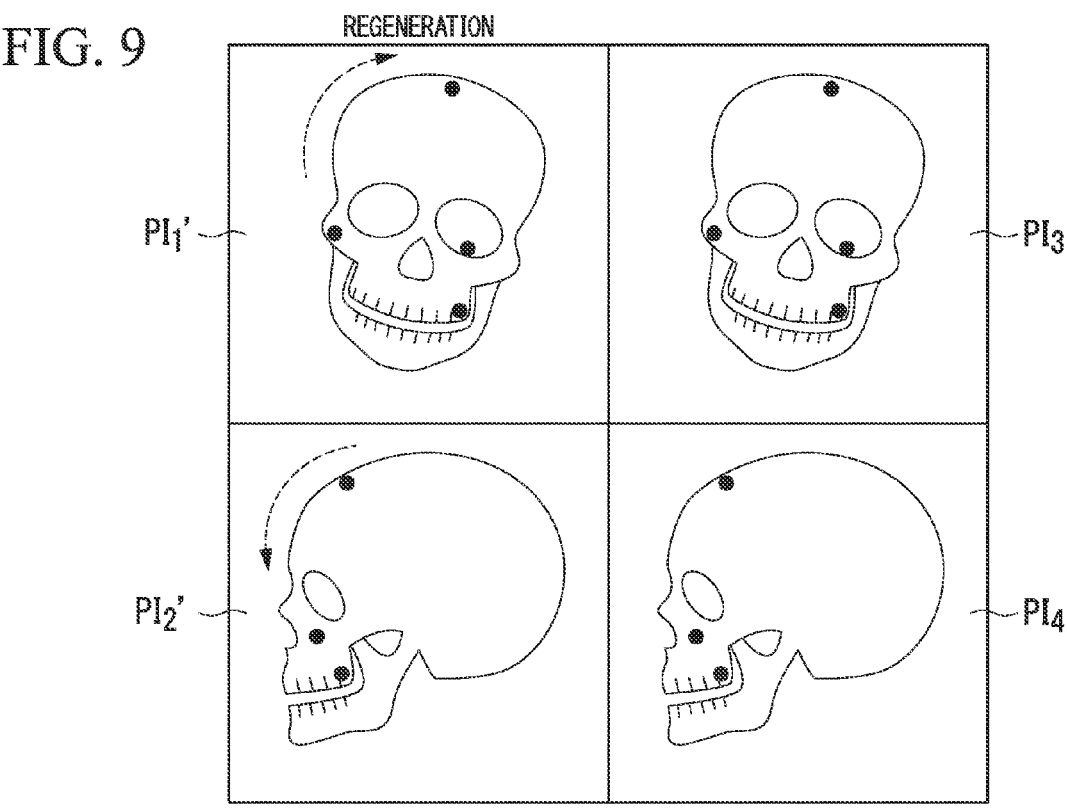
FIG. 9 illustrates another example of regeneration of first and second perspective images to be performed by the image processor according to the first embodiment.

FIGS. 8 and 9 illustrate an example of regeneration of first and second perspective images $PI_1'$ and $PI_2'$ performed by the image processor 100 according to the first embodiment. Specifically, FIG. 8 illustrates an example of first to fourth perspective images $PI_1$ to $PI_4$ when at least one group of corresponding points are input. FIG. 9 illustrates an example of first to fourth perspective images $PI_1'$, $PI_2'$, $PI_3$, and $PI_4$ after the corresponding points are input. As shown in FIG. 9, the target A on the first and second perspective images $PI_1'$ and $PI_2'$ regenerated from the three-dimensional volume data Vd shifted based on the calculated difference D is changed in such a manner as to reflect the posture of the target A on the third and fourth perspective images $PI_3$ and $PI_4$.

The image processor 100 regenerates the first and second perspective images $PI_1'$ and $PI_2'$ from the three-dimensional volume data Vd based on the calculated difference D and presents the regenerated perspective images $PI_1'$ and $PI_2'$ to the user. Thus, it is possible to present to the user, the first and second perspective images $PI_1'$ and $PI_2'$ respectively similar to the third and fourth perspective images $PI_3$ and $PI_4$. Additionally, corresponding points can be designated on the regenerated first and second perspective images $PI_1'$ and $PI_2'$ respectively similar to the third and fourth perspective images $PI_3$ and $PI_4$, thereby making it easier for the user to designate the corresponding points.

Here, the display image generator 115 of the first embodiment may overlay-display on the first to fourth perspective images $PI_1'$, $PI_2'$, $PI_3$, and $PI_4$, an epipolar line L corresponding to the corresponding points (first and second groups of points $S_1$ and $S_2$) input by the user, as shown in FIGS. 7 and 8. Additionally, the displayed position of the epipolar line L to be overlay-displayed on the first and second perspective images $PI_1$ and $PI_2$ may be modified in accordance with the difference D.

Additionally, the display image generator 115 of the first embodiment may include combined images $I_1$ and $I_2$ in the display image DI including the first to fourth perspective images $PI_1$ to $PI_4$. The combined image $I_1$ is obtained by combining the first and third perspective images $PI_1$ and $PI_3$, thus superimposing on the combined image $I_1$, the corresponding points of the first group of points $S_1$ on the first perspective image $PI_1$ and the corresponding points of the second group of points $S_2$ on the third perspective image $PI_3$.

The combined image $I_2$ is obtained by combining the second and fourth perspective images $PI_2$ and $PI_4$, thus superimposing on the combined image $I_2$, the corresponding points of the first group of points $S_1$ on the second perspective image $PI_2$ and the corresponding points of the second group of points $S_2$ on the fourth perspective image $PI_4$.

Figure 10:
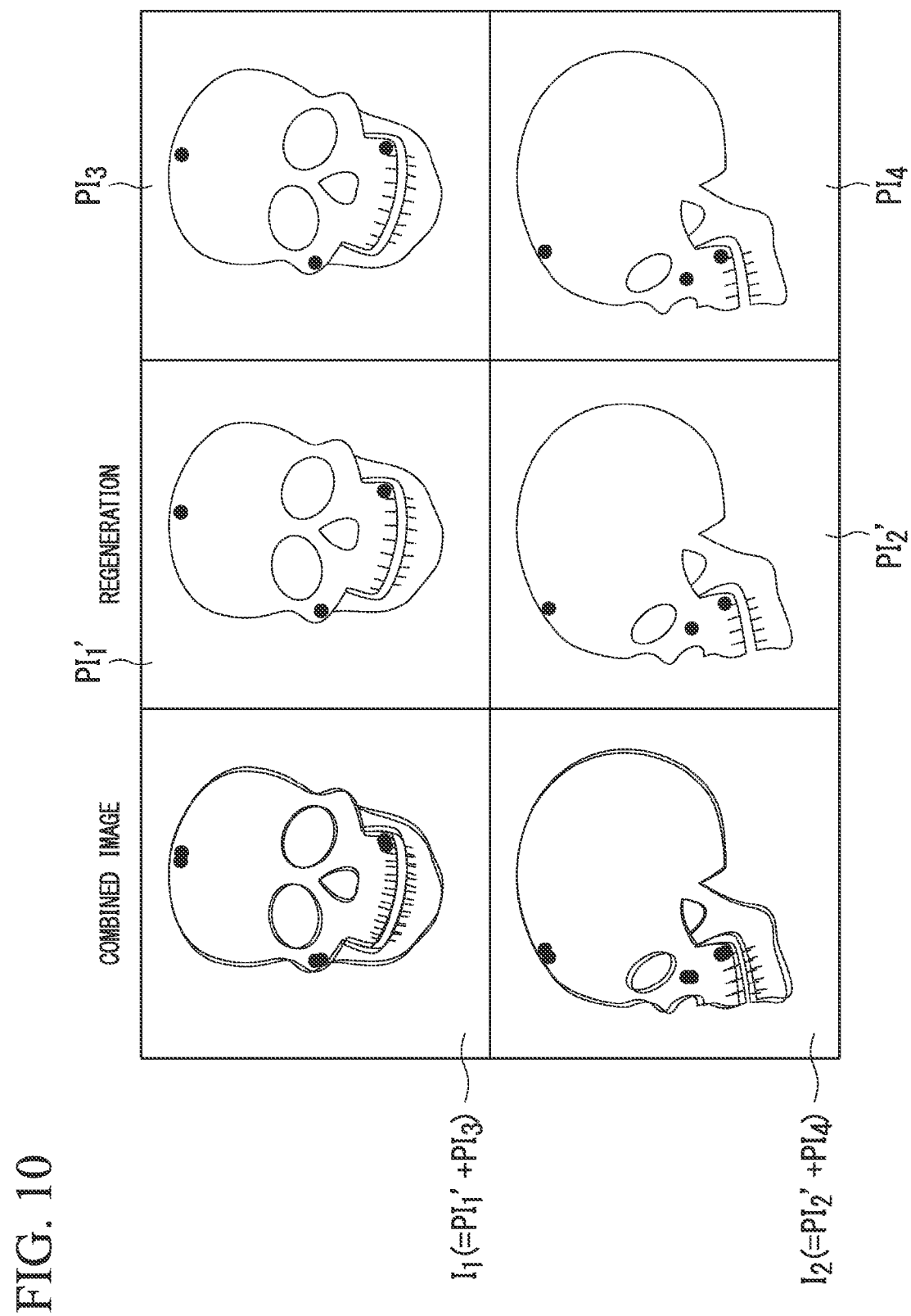
FIG. 10 illustrates an example of a display image including combined images according to the first embodiment.

FIG. 10 is a diagram illustrating an example of the position of the display image DI including the combined images $I_1$ and $I_2$ according to the first embodiment. As shown in FIG. 10, the combined images $I_1$ and $I_2$ are included in the display image DI such that the combined image $I_1$, the first perspective image $PI_1'$, and the third perspective image $PI_3$ are aligned, and the combined image $I_2$, the first perspective image $PI_2'$, and the third perspective image $PI_4$ are aligned. Thus, the combined images $I_1$ and $I_2$ are displayed with the perspective images $PI_1'$, $PI_2'$, $PI_3$, and $PI_4$, thereby making it possible for the user to recognize the difference in position of the target A between at the planning time and at the treatment time. Thus, it is possible for the user to easily designate corresponding points.

Regarding the positioning process performed by the image processor 100 of the first embodiment, descriptions have been given with respect to the configuration such that it is determined whether or not input of corresponding points by the user has been complete (step S109), thereby repeatedly performing calculation of the difference D, regeneration of the first and second perspective images $PI_1'$ and $PI_2'$, an update of coordinates of the first group of points $S_1$. However, the configuration is not limited thereto. For example, the configuration may be such that the calculation of the difference D, the regeneration of the first and second perspective images $PI_1'$ and $PI_2'$, the update of coordinates of the first group of points $S_1$, may be performed one or a predetermined number of times without performing the process of determining whether or not the input of corresponding points has been complete (step S109).

Additionally, the corresponding point acquirer 112 of the first embodiment may determines, when a new corresponding point is input through operations by the user, whether or not the input of the new corresponding point is to modify the already-input corresponding point, and delete the already-input corresponding point if it is determined that the input of the new corresponding point is to modify the already-input corresponding point. The determination of whether or not the input of the new corresponding point is to modify the already-input corresponding point is performed by, for example, using a predetermined threshold value. If the distance between the newly-input corresponding point and the already-input corresponding point is less than the predetermined threshold value, the corresponding point acquirer 112 determines that the input of the new corresponding point is to modify the already-input corresponding point, and deletes the already-input corresponding point closest to the newly-input corresponding point. Thus, by determining whether or not the input of the new corresponding point is to modify the already-input corresponding point, it is possible to easily modify the already-input corresponding point when a new corresponding point is input.

Further, the corresponding point acquirer 112 of the first embodiment may not only acquire a new corresponding point and modify the already-captured corresponding point, but also receive an instruction to delete a corresponding point. Moreover, the configuration may be such that when the corresponding point acquirer 112 deletes a corresponding point, the processes subsequent to step S105 in the positioning process are performed again based on the remaining corresponding points (first and second groups of points $S_1$ and $S_2$).

Second Embodiment

Figure 11:
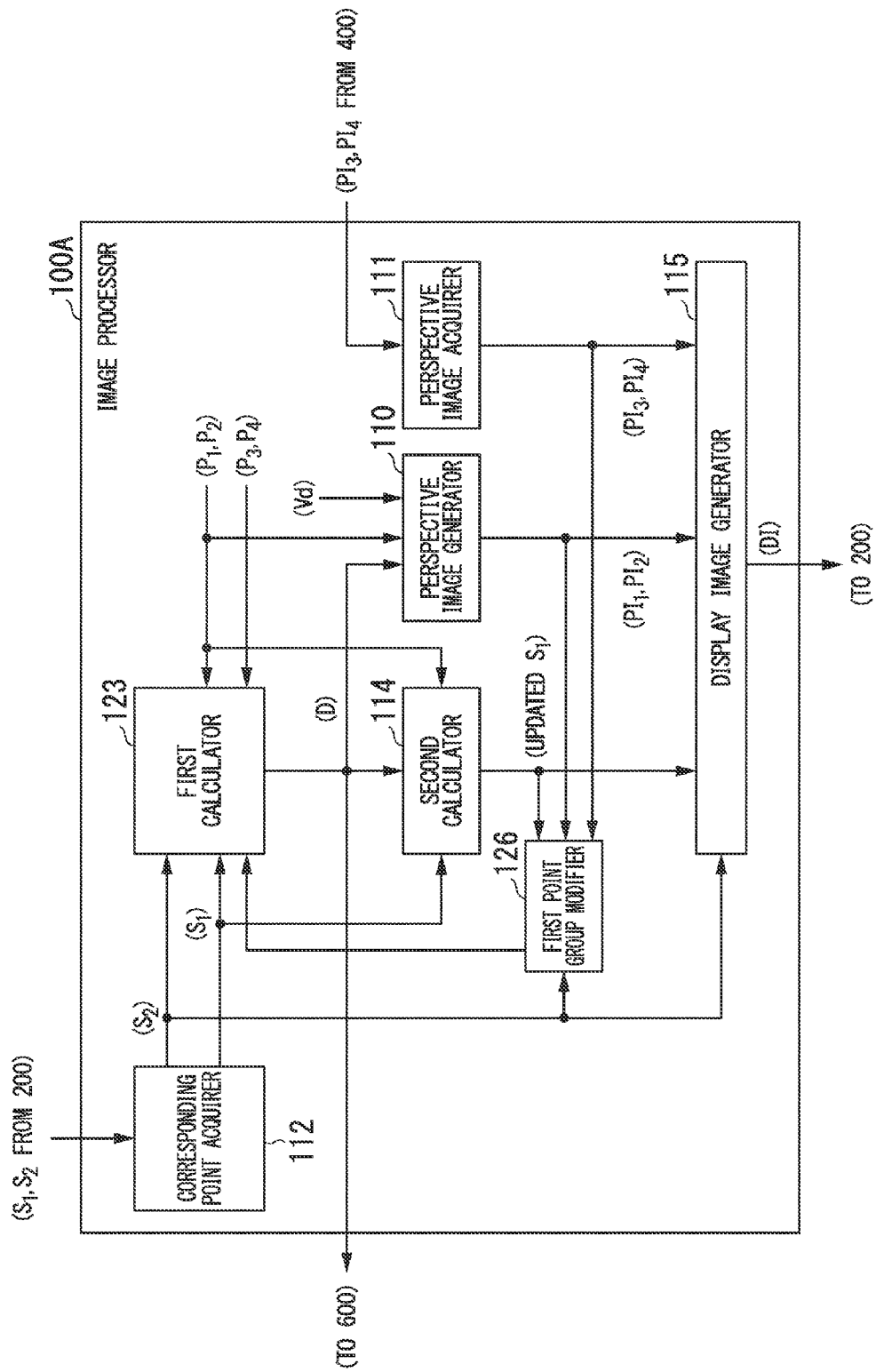
FIG. 11 is a block diagram illustrating an example of an image processor according to a second embodiment.

FIG. 11 is a block diagram illustrating an example of an image processor 100A according to a second embodiment. As shown in FIG. 11, the image processor 100A includes the perspective image generator 110, the perspective image acquirer 111, the corresponding point acquirer 112, a first calculator 123, the second calculator 114, the display image generator 115, and a first point group modifier 126. The image processor 100A of the second embodiment differs from the image processor 100 of the first embodiment (shown in FIG. 2) in that the image processor 100A includes the first calculator 123 in lieu of the first calculator 113 and further includes the first point group modifier 126. Hereinafter, same reference numerals represent structural elements between the image processors 100 and 100A, and explanations thereof are omitted.

Similar to the first calculator 113 of the first embodiment, the first calculator 123 of the second embodiment calculates a difference D in position of the target A based on the first and second groups of points $S_1$ and $S_2$, and the first to fourth parameters $P_1$ to $P_4$. Here, when there is a first group of points whose coordinates are modified by the first point group modifier 126, the first calculator 123 of the second embodiment uses the first group of points modified and output from the first point group modifier 126. Otherwise, the first calculator 123 uses the first group of points acquired by the corresponding point acquirer 112.

The first point group modifier 126 receives the first group of points $S_1$ whose coordinates have been updated by the second calculator 114, the second group of points $S_2$ acquired by the corresponding point acquirer 112, the first and second perspective images $PI_1$ and $PI_2$ generated by the perspective image generator 110, and the third and fourth perspective images $PI_3$ and $PI_4$ acquired by the perspective image acquirer 111. The first point group modifier 126 modifies the updated coordinates of the first group of points S based on the first to fourth perspective images $PI_1$ to $PI_4$ and generates the modified coordinates of the first group of points $S_1$.

Hereinafter, the modifying process to be performed by the first point group modifier 126 is explained in detail. The first point group modifier 126 captures a partial image $r^{(3)}$ having the predetermined size and a center at the n-th corresponding point $(u_n^{(3)}, v_n^{(3)})$ (n=1, ..., N) on the third perspective image $PI_3$, which is included in the second group of points $S_2$. Here, N is the number of groups of corresponding points acquired by the corresponding point acquirer 112. Additionally, the first point group modifier 126 captures a partial image $r^{(1)}$ having a predetermined size and a center at the n-th corresponding point $(u_n^{(1)}, v_n^{(1)})$ (n=1, ..., N) on the first perspective image $PI_1$, which is included in the first group of points $S_1$.

The first point group modifier 126 calculates a similarity C between the partial images $r^{(1)}$ and $r^{(3)}$. The similarity is calculated by, for example, normalized cross correlation shown in the following Expression (21).

$$C = \frac{\sum_{v \in r}\sum_{u \in r}((I_1(u_n^{(1)}, v_n^{(1)}) - \bar{I}_1^r)(I_3(u_n^{(3)}, v_n^{(3)}) - \bar{I}_3^r))}{\sqrt{\sum_v\sum_u\left((I_1(u_n^{(1)}, v_n^{(1)}) - \bar{I}_1^r)^2 \sum_v\sum_u I_3(u_n^{(3)}, v_n^{(3)}) - \bar{I}_3^r\right)^2}} \quad (21)$$

In Expression (21), C represents the similarity. As the similarity C becomes closer to 1, the similarity between the partial images $r^{(1)}$ and $r^{(3)}$ becomes higher. As the similarity C becomes closer to −1, the similarity between the partial images $r^{(1)}$ and $r^{(3)}$ becomes lower. $I_j(u, v)$ represents a pixel value of the j-th perspective image $PI_j$ (j=1, 2, 3, 4). u and v represent elements of a coordinate of a point included in an image region $r^{(j)}$. $\overline{I_j^r}$ represents an average of values of pixels included in the image region r(j) on the j-th perspective image $PI_j$.

Similarly, the first point group modifier 126 calculates a similarity C between partial images $r^{(2)}$ and $r^{(4)}$. A partial image $r^{(2)}$ has a predetermined size and a center at the n-th corresponding point $(u_{11}^{(2)}, v_{11}^{(2)})$ (n=1, ..., N) on the second perspective image $PI_2$, which is included in the first group of points $S_1$. The partial image $r^{(4)}$ has a predetermined size and a center at the n-th corresponding point $(u_n^{(4)}, v_n^{(4)})$(n=1, ..., N) on the fourth perspective image $PI_4$, which is included in the second group of points $S_2$.

The first point group modifier 126 determines whether or not the similarity C calculated with respect to each corresponding point included in the first group of points $S_1$ is greater than or equal to a predetermined reference value. Then, the first point group modifier 126 determines to be a point to be modified, the corresponding point of the first group of points $S_T$, which has the similarity C that is smaller than the reference value.

The first point group modifier 126 captures, as a template, a partial image having a predetermined size and a center at the n-th corresponding point $(u_n^{(3)}, v_n^{(3)})$ on the third perspective image $PI_3$. The n-th corresponding point $(u_n^{(3)}, v_n^{(3)})$ on the third perspective image $PI_3$ corresponds to the n-th corresponding point $(u_n^{(1)}, v_n^{(1)})$ of the first group of points $S_1$ on the first perspective image $PI_1$ which is determined to be the point to be modified. The first point group modifier 126 detects a region on the first perspective image $PI_1$, which has the highest similarity to the captured template. The first point group modifier 126 replaces the n-th corresponding point $(u_n^{(1)}, v_n^{(1)})$ corresponding to the n-th corresponding point $(u_n^{(3)}, v_n^{(3)})$ with a center point of the region detected on the first perspective image $PI_1$, thus modifying the coordinates of the first group of points $S_1$. Here, the similarity to the template may be calculated by the normalized cross correlation or another method.

Thus, the first point group modifier 126 determines whether or not there is a corresponding point of the first group of points $S_1$ which requires modification. If there is a corresponding point of the first group of points $S_1$ which requires modification, the first point group modifier 126 modifies the coordinate of the corresponding point on the first or second perspective images $PI_1$ or $PI_2$. When the modification is made, the first point group modifier 126 supplies the modified first group of points $S_1$ to the first calculator 123.

Figure 12:
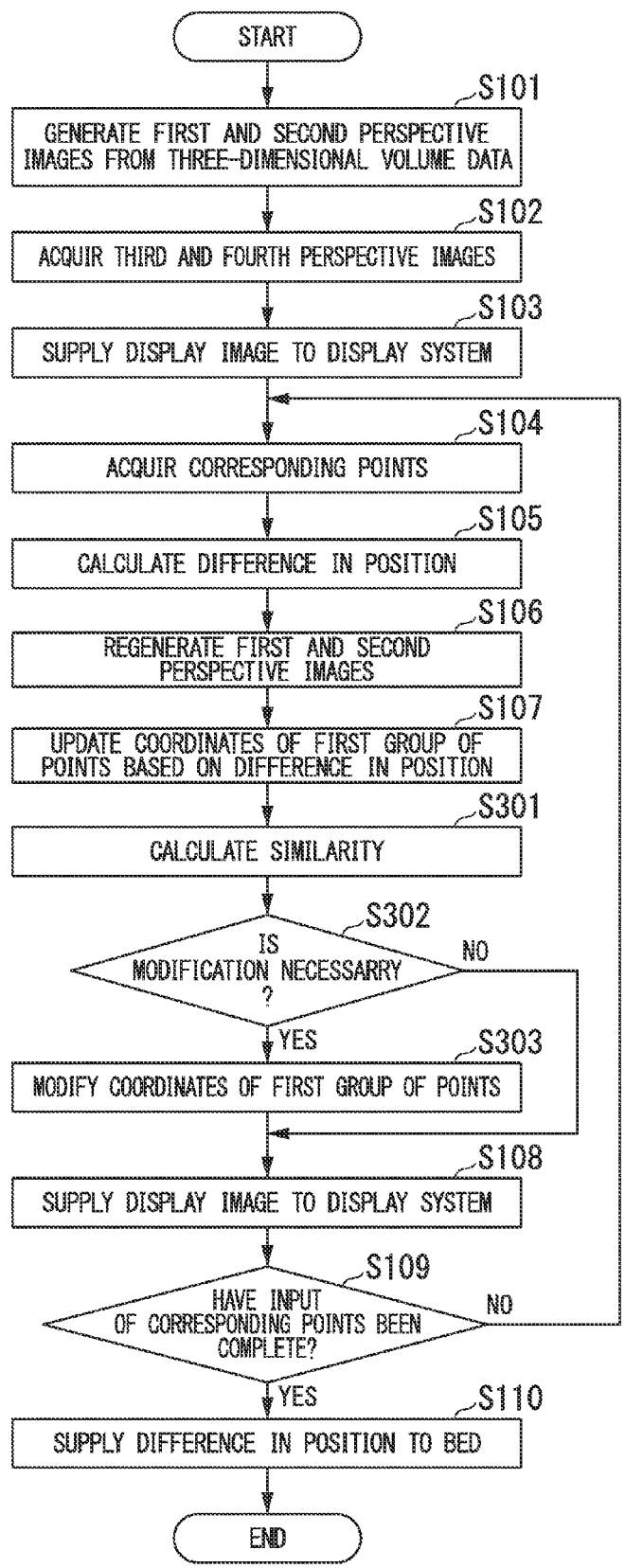
FIG. 12 is a flowchart illustrating a positioning process to be performed by the image processor according to the second embodiment.

FIG. 12 is a flowchart illustrating a positioning process to be performed by the image processor 100A according to the second embodiment. The positioning process to be performed by the image processor 100A of the second embodiment differs from the positioning process to be performed by the image processor 100 of the first embodiment (shown in FIG. 3) in that steps S301 to S303 are provided between steps 107 and S108. Hereinafter, same reference numerals represent same steps between the positioning processes of the first and second embodiments and explanations thereof are omitted.

After the second calculator 114 updates the coordinates of the first group of points $S_1$ in step S107, the first point group modifier 126 calculates the similarity C with respect to each corresponding point included in the updated first group of points $S_1$ (step S301).

The first point group modifier 126 compares to a reference value, the similarity C with respect to each corresponding point included in the first group of points $S_1$, thereby determining whether or not the corresponding point requires modification (step S302). If all the corresponding points require no modification (step S302: NO), the first point group modifier 126 proceeds to step S108.

If there is a corresponding point requiring modification (step S302: YES), the first point group modifier 126 performs the aforementioned modifying process on the corresponding point requiring modification, and supplies the modified first group of points $S_1$ to the first calculator 123 (step S303). Then, the first point group modifier 126 proceeds to step S108.

As explained above, according to the image processor 100A of the second embodiment, the first point group modifier 126 determines whether or not there is a corresponding point of the first group of points $S_1$ which requires modification for such a reason that a corresponding point of the updated first group of points is deviated. This determination is made based on the similarity C between the partial images $r^{(1)}$ and $r^{(3)}$ or between the partial images $r^{(2)}$ and $r^{(4)}$. When there is a corresponding point of the first group of points $S_1$ which requires modification, a coordinate of the corresponding point is modified. When deviation occurs to a corresponding point of the first group of points $S_1$ which is on the regenerated first or second perspective images $PI_1'$ or $PI_2'$, the coordinate of the deviated corresponding point is modified, thereby preventing deviation from occurring among the two corresponding points designated respectively on the first and second perspective images $PI_1$ and $PI_2$, and the two corresponding points designated respectively on the third and fourth perspective images $PI_3$ and $PI_4$. Thus, it is possible for the user to easily compare the first to fourth perspective images $PI_1$ to $PI_4$, and perform confirmation or modification of the corresponding points. The first point group modifier 126 is an example of a corresponding point modifier that calculates the above described similarity between the first and second partial images.

Here, the aforementioned possible structural modifications applicable to the image processor 100 of the first embodiment are also applicable to the image processor 100A of the second embodiment.

Third Embodiment

Figure 13:
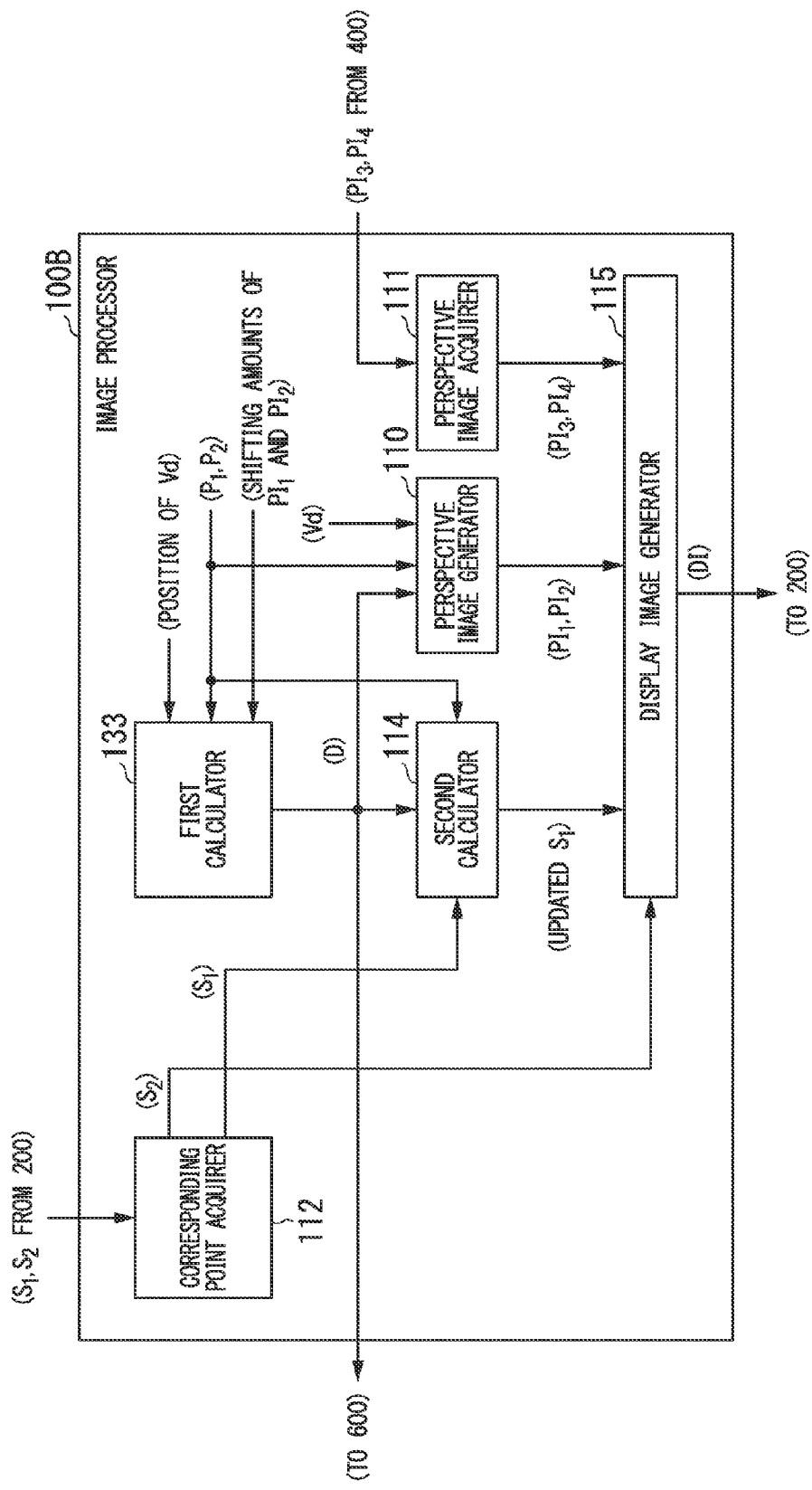
FIG. 13 is a block diagram illustrating an example of an image processor according to a third embodiment.

FIG. 13 is a block diagram illustrating an example of an image processor 100B according to a third embodiment. As shown in FIG. 13, the image processor 100B includes the perspective image generator 110, the perspective image acquirer 111, the corresponding point acquirer 112, a first calculator 133, the second calculator 114, and the display image generator 115. The image processor 100B of the third embodiment differs from the image processor 100 of the first embodiment (shown in FIG. 2) in that the image processor 100B includes the first calculator 133 in lieu of the first calculator 113. Hereinafter, same reference numerals represent same structural elements between the image processors 100 and 100B, and explanations thereof are omitted.

The first calculator 133 receives the shifting amount of the first or second perspective image $PI_1$ or $PI_2$ based on an input received through operations by a user, the first and second parameters $P_1$ and $P_2$, and the position of the three-dimensional volume data Vd. The position of the three-dimensional volume data Vd is a three-dimensional coordinate of the target A indicated by the three-dimensional volume data Vd or a three-dimensional coordinate of a voxel of the voxel data. The position of the three-dimensional volume data Vd is data captured at the time the three-dimensional volume data Vd is captured. The shifting amount of the first or second perspective image $PI_1$ or $PI_2$ is input by, for example, the user operating the operation device 220 based on the first to fourth perspective images $PI_1$ to $PI_4$ displayed on the display system 200.

Figure 15:
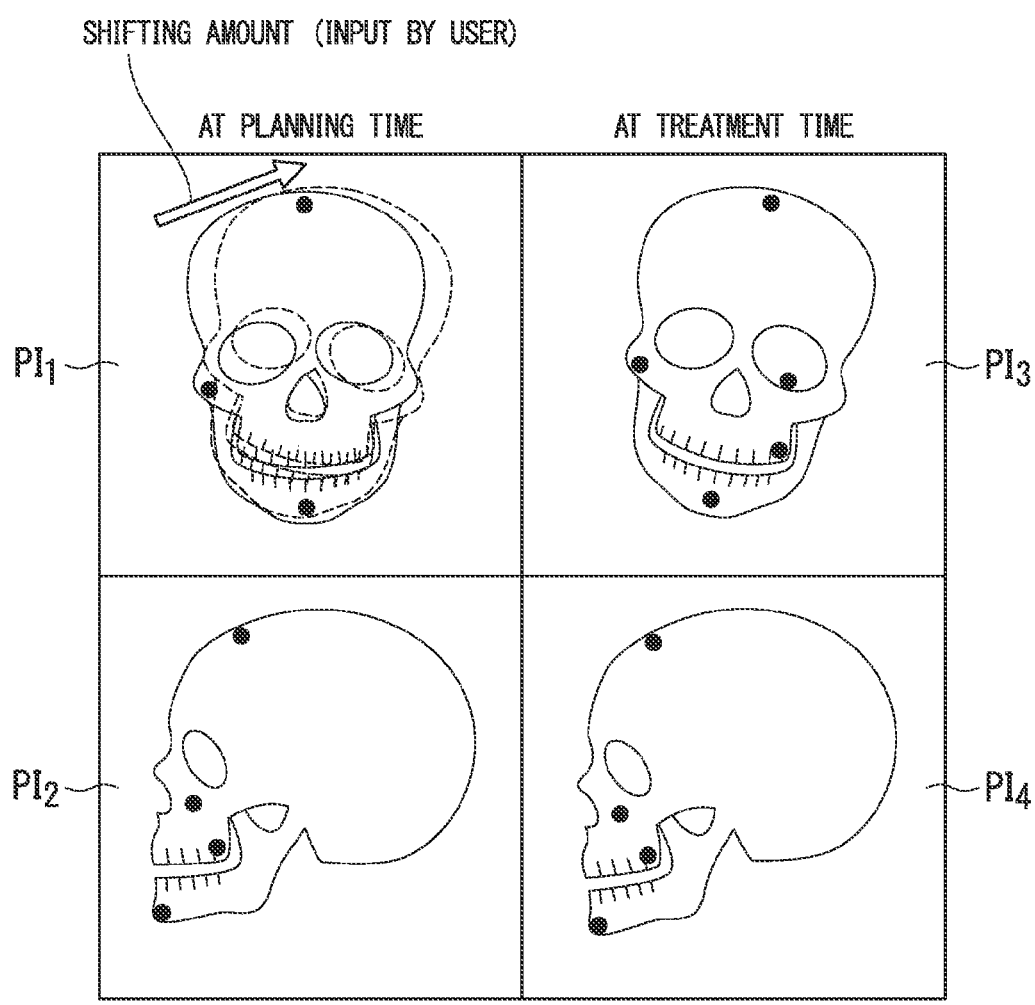
FIG. 15 illustrates images showing an example of the input shifting amount of a first perspective image according to the third embodiment.

FIG. 15 illustrates images showing an example of the shifting amount of the first perspective image $PI_1$ according to the third embodiment. As shown in FIG. 15, the user performs operation that shifts the first perspective image $PI_1$ while comparing the first to fourth perspective images $PI_1$ to $PI_4$ displayed by the display system 200. Thus, the shifting amount of the first perspective image $PI_1$ is input to the operation device 220. In this case, the first calculator 133 receives the shifting amount of the first perspective image $PI_1$ received by the operation device 220.

Figure 14:
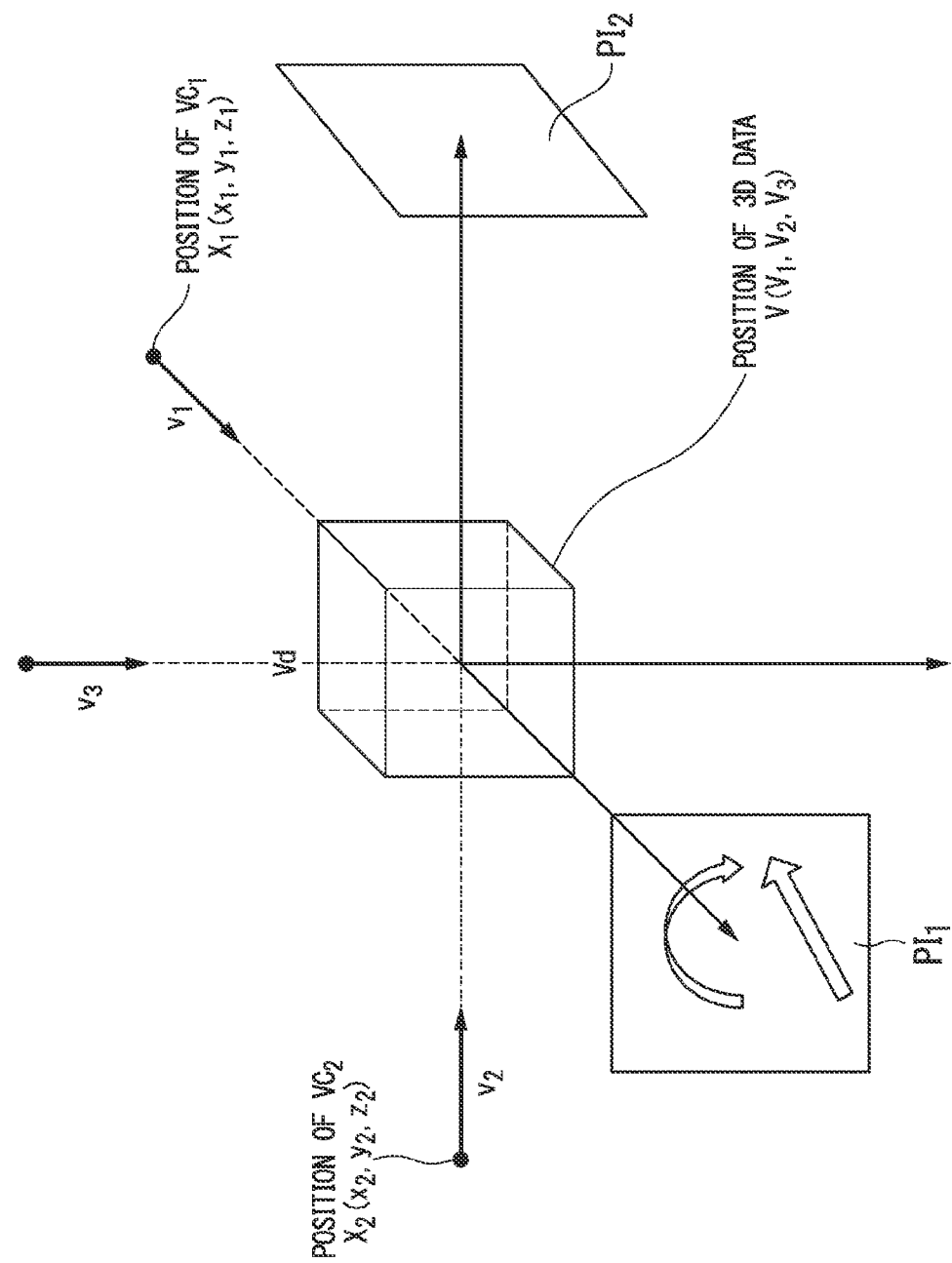
FIG. 14 illustrates a positional relationship among three-dimensional volume data, and the first and second perspective images, which are used for a first calculator of the third embodiment to calculate difference.

The first calculator 133 calculates a difference D in position of the target A between at the planning time and at the treatment time, based on the shifting amount of the first or second perspective image $PI_1$ or $PI_2$ input by the user. Hereinafter, a process for the first calculator 133 to calculate the difference D is explained in detail. FIG. 14 illustrates a positional relationship among the three-dimensional volume data Vd, and the first and second perspective images $PI_1$ and $PI_2$, which are used for the first calculator 133 of the third embodiment to calculate the difference D.

In FIG. 14, a virtual camera $VC_1$ represents a camera that captures a first perspective image $PI_1$. A virtual camera $VC_2$ represents a camera that captures a second perspective image $PI_2$. The position of the virtual camera $VC_1$ in the three-dimensional space is represented as $X_1=(x_1, y_1, z_1)$. The position of the virtual camera $VC_2$ in the three-dimensional space is represented as $X_2=(x_2, y_2, z_2)$. The position of the three-dimensional volume data Vd is represented as $V=(V_1, V_2, V_3)$. The position of the three-dimensional volume data Vd is, for example, the position of the gravity center of the three-dimensional volume data Vd. The positions of the virtual camera $VC_1$ and the virtual camera $VC_2$ can be obtained from the first and second parameters $P_1$ and $P_2$.

The first calculator 133 calculates the three dimensional unit vectors $v_1$, $v_2$, and $v_3$ from the position $X_1$ of the virtual camera $VC_1$, the position $X_2$ of the virtual camera $VC_2$, and the position V of the three-dimensional volume data Vd. The unit vectors $v_1$ and $v_2$ are calculated from the following Expressions (22-1) and (22-2).

$$v_1 = \frac{V - X_1}{\|V - X_1\|} \qquad (22\text{-}1)$$

$$v_2 = \frac{V - X_2}{\|V - X_2\|} \qquad (22\text{-}2)$$

The unit vector $v_3$ can be calculated as a unit normal vector to a plane defined by the unit vectors $v_1$ and $v_2$ that extend from the position V of the three-dimensional volume data Vd. The shifting amount of the first or second perspective image $PI_1$ or $PI_2$ can be expressed by the three three-dimensional unit vectors $v_1$, $v_2$, and $v_3$. For example, when the first perspective image $PI_1$ is rotated by the angle θ around the center of the first perspective image $PI_1$, the three-dimensional volume data Vd rotates by the angle θ around the unit vector $v_1$. Using the Rodrigues's formula, a rotation matrix R' can be calculated from the rotation angle around an arbitrary rotation axis. Additionally, when the first perspective image $PI_1$ is shifted by Δu in the horizontal direction of the first perspective image $PI_1$ and is shifted by Δv in the vertical direction thereof, that is, the first perspective image $PI_1$ is translated by the shifting amount (Δu, Δv), the translation vector t' can be calculated as $t'=\Delta u \cdot v_2 + \Delta v \cdot v_3$.

The rotation matrix R' and the translation vector t' represent the shifting of the position Y of the three-dimensional volume data Vd to the position X of the target A at the treatment time. For this reason, the rotation matrix R' and the translation vector t' can be converted into the rotation matrix R and the translation vector t which represent the difference D of the target A from the position X to the position Y. This conversion can be performed using the following Expressions (23-1) and (23-2).

$$R = R'^T \qquad (23\text{-}1)$$

$$t = -R'^T t' \qquad (23\text{-}2)$$

As explained above, the first calculator 133 of the third embodiment calculates the difference D of the target A (represented by the rotation matrix R and the translation vector t) based on the first or second perspective image $PI_1$ or $PI_2$ input through operations by the user. The image processor 100B calculates the difference D of the target A based on the shifting amount of the image which is input by the user based on the user's experience, thereby making it possible to easily reduce the deviation between the first and third perspective images $PI_1$ and $PI_3$ and the deviation between the second and fourth perspective images $PI_2$ and $PI_4$ when the deviations are large. The first and second perspective images $PI_1$' and $PI_2$' regenerated after the deviations are reduced are compared to each other, thereby making it possible for the user to easily designate corresponding points.

Here, the aforementioned structural modification applicable to the image processor 100 of the first embodiment is also applicable to the image processor 100B of the third embodiment.

Additionally, the image processor 100B of the third embodiment may be configured such that the first calculator 133 is not provided, and the second calculator 114 receives the difference D input through operations by the user. In this case, the difference D is determined based on the experience of the user (such as a medical doctor or a surgeon), or selected by the user from multiple predetermined candidates for the difference.

According to the image processor and the treatment system including the image processor, which are of at least one of the above embodiments, the difference D that is the difference in position of the target A between at the planning time and at the treatment time is calculated. Then, the three-dimensional volume data Vd is shifted based on the difference D. Then, the first and second perspective images $PI_1$ and $PI_2$, which are to be compared with the third and fourth perspective images $PI_3$ and $PI_4$ captured at the treatment time, are generated from the shifted three-dimensional volume data Vd. Thus, it is possible to increase the similarity among the first to fourth perspective images $PI_1$ to $PI_4$ to be compared with one another by the user, thereby making it possible for the user to easily designate corresponding points.

The configurations of the image processors of any embodiments explained above may be combined. For example, in an initial state where setting of corresponding points is initiated, after the shifting amount is received through operations by the user and the difference D is calculated in the manner explained with respect to the image processor 100B of the third embodiment, the subsequent processes may be performed in the manner explained with respect to the image processor 100 of the first embodiment or the image processor 100B of the second embodiment. By this combination, when the difference D of the target A is large, precise calculation of the difference D can be performed after the deviation among the first to fourth perspective images $PI_1$ to $PI_4$ are reduced based on the user input, thereby enabling a reduction in time required for performing the positioning process.

Additionally, the descriptions have been given in each embodiment with respect to the configuration in which the image processor generates the first and second perspective images $PI_1$ and $PI_2$ from the three-dimensional volume data Vd shifted based on the difference D. However, the image processor may be configured to, instead of shifting the three-dimensional volume data Vd based on the difference D, shift, based on the difference D, the positions of the virtual cameras $VC_1$ and $VC_2$ respectively indicated by the first and second parameters $P_1$ and $P_2$. In other words, the image processor may be configured to change, based on the difference D, the virtually-viewing direction of the first perspective image $PI_1$ and the virtually-viewing direction of the second perspective image $PI_2$.

Further, each of the above image processors may be implemented by a general semiconductor integrated circuit, or a customizable electronic circuit such as an FPGA (field programmable gate array). Also each of the above image processors may be implemented by a processor and a memory that stores processor-executable instructions that, when executed by the processor, to cause the processor to perform the above-described acts or operations for the above-described image processing.

In other cases, one or more programs for the image processor of each of the above embodiments to perform the above-described acts or operations for the above-described image processing may be stored in a computer-readable recording medium, so that a computer system can read and execute the program stored in the computer-readable recording medium, thereby performing the positioning process.

Here, the "computer system" may include software such as an OS and one or more applications and hardware such as any peripheral device. Additionally, the "computer system" may include a WWW system that provides homepage providing or displaying environments.

Further, the "computer-readable storage medium" may include any non-transitory computer-readable storage mediums such as a storage device, such as a portable medium, for example, a flexible disk, a magneto optical disk, a ROM, or a CD-ROM, or a hard disk built in a computer system. Moreover, the computer-readable storage medium may also include a medium that temporarily stores a program, such as a volatile memory included in a computer system which serves as a server or client when the program is transmitted via a network such as the Internet, or a communication line such as a telephone line.

Additionally, the above program may be transmitted from a computer system storing that program in a storage device thereof to another computer system via a transmission medium or by carrier waves passing through a transmission medium. The "transmission medium" that transmits the program may include a medium having a function of transmitting information, such as a communication network, for example, the Internet, or a communication line, for example, a telephone line. Further, the above program may include a differential program in combination with the program already stored in the computer system.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a computer including processing circuitry configured to at least:
generate a first perspective image of a target viewed in a first direction, based on three-dimensional volume data of the target;
acquire a second perspective image of the target viewed in a second direction;
acquire initial positions of one or more pairs of first and second corresponding points respectively on the first and second perspective images;
update the first direction and the position of the first corresponding point, based on the difference in position of the target between the first and second perspective images;
regenerate the first perspective image viewed in the updated first direction; and
generate a first display image including the regenerated first perspective image and the second perspective image, the updated first corresponding point on the regenerated first perspective image, and the second corresponding point on the second perspective image.

2. The apparatus according to claim 1, wherein:
the processing circuitry is configured to calculate the difference by calculating a difference in position between the three-dimensional volume data and the target at the time of capturing the target from which the second perspective image is acquired, based on the one or more first and second corresponding points of the first and second perspective images.

3. The apparatus according to claim 2, wherein the processing circuitry is configured to:
acquire one or more pairs of third and fourth corresponding points respectively on the first and second perspective images,
update the difference in position between the first and second perspective images, based on the one or more pairs of first and second corresponding points and the one or more pairs of third and fourth corresponding points,
update the positions of the one or more first and third corresponding points, based on the difference updated lastly in position between the first and second perspective images, and
generate an updated one of the first display image including the first perspective image and the one or more first and third corresponding points, which are updated lastly, and the second perspective image.

4. The apparatus according to claim 2, wherein the processing circuitry is configured to update the difference, based on one or more undeleted pairs of the first and second corresponding points acquired, when any corresponding points have been deleted.

5. The apparatus according to claim 3, wherein the processing circuitry is configured to update the difference, based on one or more undeleted pairs of the first and second corresponding points acquired, when any corresponding points have been deleted.

6. The apparatus according to claim 1, wherein the processing circuitry is configured to determine whether a designated corresponding point on one of the first and second perspective images is a modified corresponding point to which the existent one of the one or more first and second corresponding points or an additional corresponding point to be added to the existent ones of the one or more first and second corresponding points and to delete a closest existent one, to the designated corresponding point, of the one or more first and second corresponding points in a case that the designated corresponding point is the modified corresponding point.

7. The apparatus according to claim 1, wherein the processing circuitry is configured to:
calculate a similarity between first and second partial images, the first partial image including the first corresponding point which position has been last updated, the second partial image including the second corresponding point which is paired with that first corresponding point,
detect a region having a highest similarity to the second partial image from the first perspective image, if the similarity calculated is smaller than a predetermined reference value; and
modify the position of the first corresponding point based on the region detected.

8. The apparatus according to claim 1, wherein the processing circuitry is configured to modify, based on the difference, an epipolar line on the first perspective image, the epipolar line is associated with the one or more first corresponding points.

9. A treatment system comprising:
an image processing apparatus;
an irradiator that irradiates X-rays to a target;
a detector that detects X-rays transmitted through the target and makes a second perspective image of the target viewed in a second direction based on the X-rays; and
a display system,
wherein the image processing apparatus comprises a computer including processing circuitry configured to at least:
generate a first perspective image of the target viewed in a first direction, based on three-dimensional volume data of the target;
acquire the second perspective image from the detector;
acquire initial positions of one or more pairs of first and second corresponding points respectively on the first and second perspective images;
update the first direction and the position of the first corresponding point, based on the difference in position between the first and second perspective images;
regenerate the first perspective image viewed in the updated first direction; and
generate a first display image including the regenerated first perspective image and the second perspective image, the updated first corresponding point on the regenerated first perspective image, and the second corresponding point on the second perspective image,
wherein the display system displays the first display image.

10. The system according to claim 9, wherein the processing circuitry is configured to:
calculate the difference by calculating a difference in position between the three-dimensional volume data and the target at the time of capturing the target from which the second perspective image is acquired, based on the one or more first and second corresponding points of the first and second perspective images.

11. The system according to claim 10, wherein the processing circuitry is configured to:
acquire one or more pairs of third and fourth corresponding points respectively on the first and second perspective images,
update the difference in position between the first and second perspective images, based on the one or more pairs of first and second corresponding points and the one or more pairs of third and fourth corresponding points,
update the positions of the one or more first and third corresponding points, based on the difference updated lastly in position between the first and second perspective images, and
generate an updated one of the first display image including the first perspective image and the one or more first and third corresponding points, which are updated lastly, and the second perspective image.

12. The system according to claim 10, wherein the processing circuitry is configured to update the difference, based on one or more undeleted pairs of the first and second corresponding points acquired, when any corresponding points have been deleted.

13. The system according to claim 11, wherein the processing circuitry is configured to update the difference, based on one or more undeleted pairs of the first and second corresponding points acquired, when any corresponding points have been deleted.

14. The system according to claim 9, wherein the processing circuitry is configured to determine whether a designated corresponding point on one of the first and second perspective images is a modified corresponding point to which the existent one of the one or more first and second corresponding points or an additional corresponding point to be added to the existent ones of the one or more first and second corresponding points and to delete a closest existent one, to the designated corresponding point, of the one or more first and second corresponding points in a case that the designated corresponding point is the modified corresponding point.

15. The system according to claim 9, wherein the processing circuitry is configured to:
calculate a similarity between first and second partial images, the first partial image including the first corresponding point which position has been last updated, the second partial image including the second corresponding point which is paired with that first corresponding point,
detect a region having a highest similarity to the second partial image from the first perspective image, if the similarity calculated is smaller than a predetermined reference value; and
modify the position of the first corresponding point based on the region detected.

16. The system according to claim 9, wherein the processing circuitry is configured to modify, based on the difference, an epipolar line on the first perspective image, the epipolar line is associated with the one or more first corresponding points.

17. An image processing method comprising:
generating a first perspective image of a target viewed in a first direction, based on three-dimensional volume data of the target;
acquiring a second perspective image of the target viewed in a second direction;
acquiring initial positions of one or more pairs of first and second corresponding points respectively on the first and second perspective images;
updating the first direction and the position of the first corresponding point, based on the difference in position of the target between the first and second perspective images;
regenerating the first perspective image viewed in the updated first direction; and
generating a first display image including the regenerated first perspective image and the second perspective image, the updated first corresponding point on the regenerated first perspective image, and the second corresponding point on the second perspective image.

18. The image processing method according to claim 17, further comprising:
calculating the difference by calculating a difference in position between the three-dimensional volume data and the target at the time of capturing the target from which the second perspective image is acquired, based on the one or more first and second corresponding points of the first and second perspective images;
acquiring one or more pairs of third and fourth corresponding points respectively on the first and second perspective images;
updating the difference in position between the first and second perspective images, based on the one or more pairs of first and second corresponding points and the one or more pairs of third and fourth corresponding points;
updating the positions of the one or more first and third corresponding points, based on the difference updated lastly in position between the first and second perspective images; and
generating an updated one of the first display image including the first perspective image and the one or more first and third corresponding points, which are updated lastly, and the second perspective image.

* * * * *